United States Patent [19]
Cramer et al.

[11] Patent Number: 5,885,231
[45] Date of Patent: Mar. 23, 1999

[54] DIGITAL MOTOR EVENT RECORDING SYSTEM

[75] Inventors: Steven C. Cramer, Brookline; Seth P. Finklestein, Needham, both of Mass.

[73] Assignee: The General Hospital Corporation, Boston, Mass.

[21] Appl. No.: 779,766

[22] Filed: Jan. 7, 1997

[51] Int. Cl.$^6$ ..................................................... A61B 5/103
[52] U.S. Cl. ........................................... 600/595; 600/587
[58] Field of Search ................................... 600/587, 595; 73/379.01, 379.02

[56] References Cited

U.S. PATENT DOCUMENTS

| | | | |
|---|---|---|---|
| 4,949,729 | 8/1990 | Haski | 600/587 |
| 5,042,503 | 8/1991 | Torok et al. | 600/595 |
| 5,131,401 | 7/1992 | Westenskow et al. | 600/595 |
| 5,166,462 | 11/1992 | Suzuki et al. | 600/595 |
| 5,263,490 | 11/1993 | Hayes et al. | 600/595 |
| 5,265,619 | 11/1993 | Comby et al. | 600/595 |
| 5,275,174 | 1/1994 | Cook | 600/587 |
| 5,471,996 | 12/1995 | Boatright et al. | 600/595 |
| 5,579,783 | 12/1996 | Naoi et al. | 600/595 |
| 5,713,370 | 2/1998 | Cook et al. | 600/595 |
| 5,749,372 | 5/1998 | Allen et al. | 600/595 |
| 5,785,666 | 7/1998 | Costello et al. | 600/595 |

OTHER PUBLICATIONS

Bütefisch et al., "Repetitive training of isolated movements improves the outcome of motor rehabilitation of the centrally paretic hand," *J. Neurol. Sci.*, 130:59–68, 1995.

Corcos et al., "Strength in Parkinson's Disease: Relationship to Rate of Force Generation and Clinical Status," *Annal. Neurol.*, 39(1):79–88, 1996.

Duncan et al., "Measurement of Motor Recovery After Stroke, Outcome Assessment and Sample Size Requirements," *Stroke*, 23(8):1084–1089, 1992.

Frischer, "Voluntary vs Autonomous Control of Repetitive Finger Tapping in a Patient with Parkinson's Disease," *Neuropsychologia*, 27(10):1261–1266, 1989.

Granger et al., "Measurement of Stroke Rehabilitation Outcome in the 1980s," *Stroke*, 21(suppl. II):II–46—II–47, 1990.

Heller et al., "Arm function after stroke: measurement and recovery over the first three months," *J. Neurol., Neurosurg., & Psych.*, 50:714–719, 1987.

Jebsen et al., "An Objective and Standardized Test of Hand Function," *Archives of Phys. Med. & Rehab.*, 311–319, 1969.

Kellor et al., "Hand Strength and Dexterity," *Am. J. Occupational Ther.*, 25(2):77–83, 1971.

Kirschner et al., "Reliability of Finger and Foot Tap Tests on Normal and Amyotrophic Lateral Sclerosis Subjects," *Phys. Ther.*, Annual Conference, San Antonio, TX, R–138, pp. 768, 1987.

Lincoln et al., "Assessment of Motor Function in Stroke Patients," *Physiotherapy*, 65(2:48–51, 1979.

(List continued on next page.)

*Primary Examiner*—Max Hindenburg
*Assistant Examiner*—Charles Marmor, II
*Attorney, Agent, or Firm*—Fish & Richardson P.C.

[57] ABSTRACT

The invention features apparatus and methods for measuring motor events of a subject, e.g., a human subject, where the motor events have a force component or both a frequency and force component. The apparatus include a transducer, adapted to generate an analog signal corresponding to frequency and/or force of the subject's motor event, e.g., a repetitive motion; an amplifier, which amplifies the analog signal; an analog-to-digital (A/D) converter, which converts the analog signal into a digital signal; and a computer. The computer is programmed to receive the digital signal as input, store the digital signal for subsequent retrieval, retrieve the stored digital signal for processing, and process the stored digital signal. The processing includes the measurement of mean force amongst the set of individual motor events over time and measurement of the mean frequency of the set of individual motor events over time.

32 Claims, 18 Drawing Sheets

OTHER PUBLICATIONS

Malouin et al., "Evaluating Motor Recovery Early After Stroke: Comparison of the Fugl–Meyer Assessment and the Motor Assessment Scale," *Arch. Phys. Med. Rehabil.*, 75:1206–1212, 1994.

Mawson, "Measuring Physiotherapy Outcome in Stroke Rehabilitation," *Physiotherapy*, 79(11):762–765, 1993.

McCulloch et al., "Upper extremity functional assessment in traumatically brain–injured patients," *J. Head Trauma Rehabil.*, 5(4):1–12, 1990.

Pinter et al., "Quantification of motor deficit in Parkinson's disease with a motor performance test series," *J. Neural Transm.* [P–D Sect.], 4:131–141, 1992.

Shimoyama et al., "The Finger–Tapping Test, A Quantitive Analysis," *Arch. Neurol.*, 47(6):681–684, 1990.

Shimoyama et al. "Microcomputer Analysis of Finger Tapping as a Measure of Cerebellar Dysfunction," *JAMA*, 251(6):724, 1984 (Abstract).

Spreen and Strauss, Chapter 10: "Motor Tests," *A Compendium of Neuropsychological Tests*, pp. 361–385, 1991.

Trombly, "Evaluation of Biomechanical and Physiological Aspects of Motor Performance," *Occup. Ther. for Phys. Dysfunction*, 4th Ed., Catherine A. Trombly, Editor, Chap. 6, pp. 150–156, 1995.

Wade et al, "The hemiplegic arm after stroke: measurement and recovery," *J. Neurol., Neurosurg., & Psych.*, 46:521–524, 1983.

"MacLab™ Data Acquistion for the Macintosh," pp. 52–55, and Transducers and Sensors, pp. 56–57, Stoelting Co. product catalogue, 1994.

*How to Turn Your Students into Laboratory Animals*, MacLab® instructional product brochure, pp. 1–19, AD Instruments, Milford, MA, 1994.

C.B. Sciences, Inc.'s "ETH–200, Two Channel Transducer Interface," product specification sheet, 1991.

"Calibration Certificate Installation Information," product specification sheet for Sealed Super–Mini Load Cell, Interface, Inc., Scottsdale, AZ, 1996.

LINEAR FIT: Par/G SSqFmax = -0.314 + 0.01841 FM

SUMMARY OF FIT:
    RSquare = 0.760
    R       = 0.872

ANALYSIS OF VARIANCE

| SOURCE | DF | Sum of Squares | Mean Square | F Ratio |
|---|---|---|---|---|
| MODEL | 1 | 2.0274970 | 2.02750 | 57.1084 |
| ERROR | 18 | 0.6390468 | 0.03550 | Prob>F |
| C TOTAL | 19 | 2.6665438 | | <.0001 |

PARAMETER ESTIMATES

| TERM | Estimate | Std Error | t Ratio | Prob>|t| |
|---|---|---|---|---|
| INTERCEPT | -0.313974 | 0.120951 | -2.60 | 0.0183 |
| FM | 0.0184056 | 0.002436 | 7.56 | <.0001 |

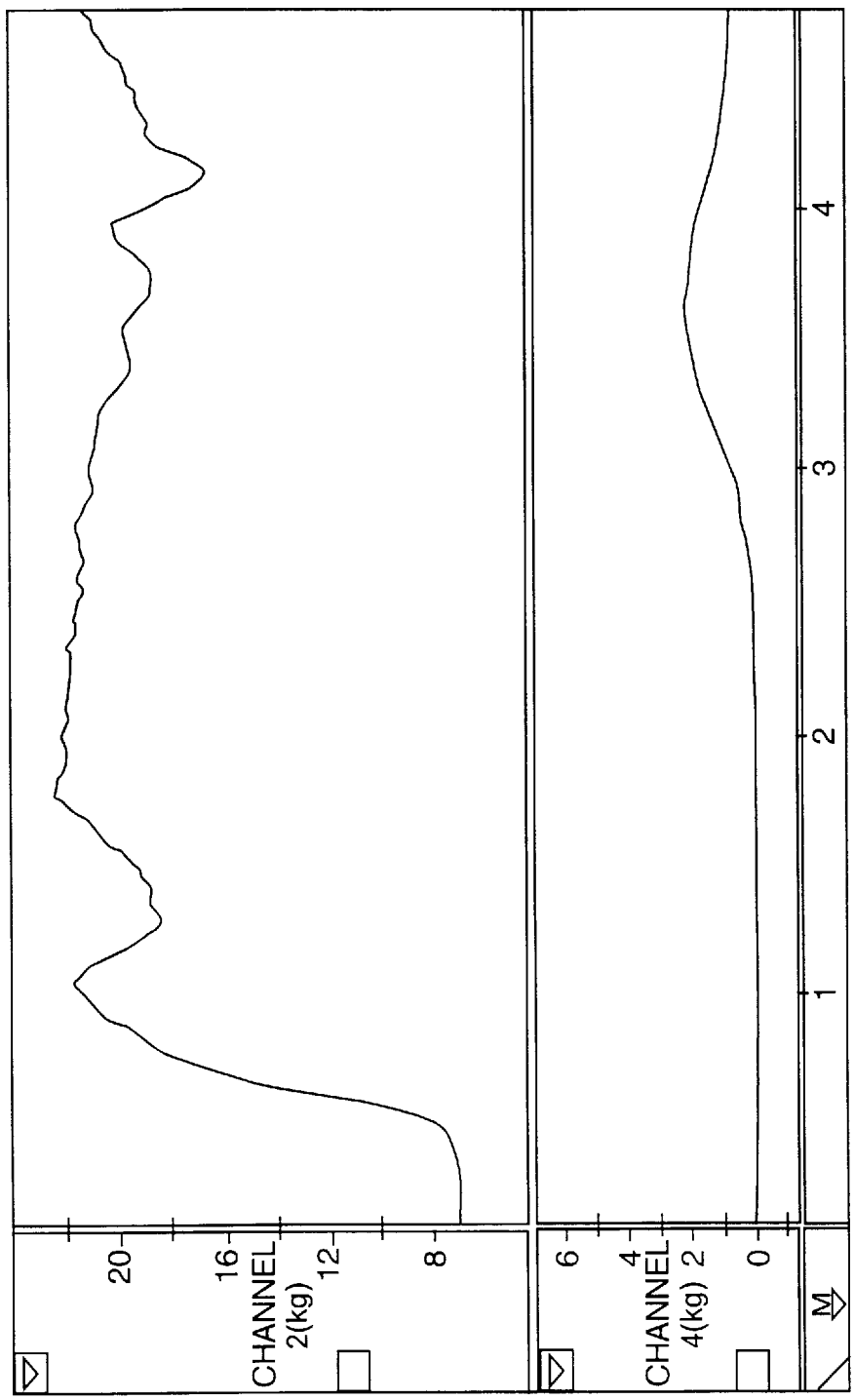

LINEAR FIT: Par/GIFrM = 0.00553 + 0.03487 FM-Hand

SUMMARY OF FIT:
    RSquare    0.668
    R    0.817

ANALYSIS OF VARIANCE

| SOURCE | DF | Sum of Squares | Mean Square | F Ratio |
|---|---|---|---|---|
| MODEL | 1 | 1.0631639 | 1.06316 | 16.0824 |
| ERROR | 8 | 0.5288570 | 0.06611 | Prob>F |
| C TOTAL | 9 | 1.5920209 | | 0.0039 |

PARAMETER ESTIMATES

| TERM | Estimate | Std Error | t Ratio | Prob>|t| |
|---|---|---|---|---|
| INTERCEPT | 0.00553 | 0.18803 | 0.03 | 0.9773 |
| FM-Hand | 0.0348675 | 0.008694 | 4.01 | 0.0039 |

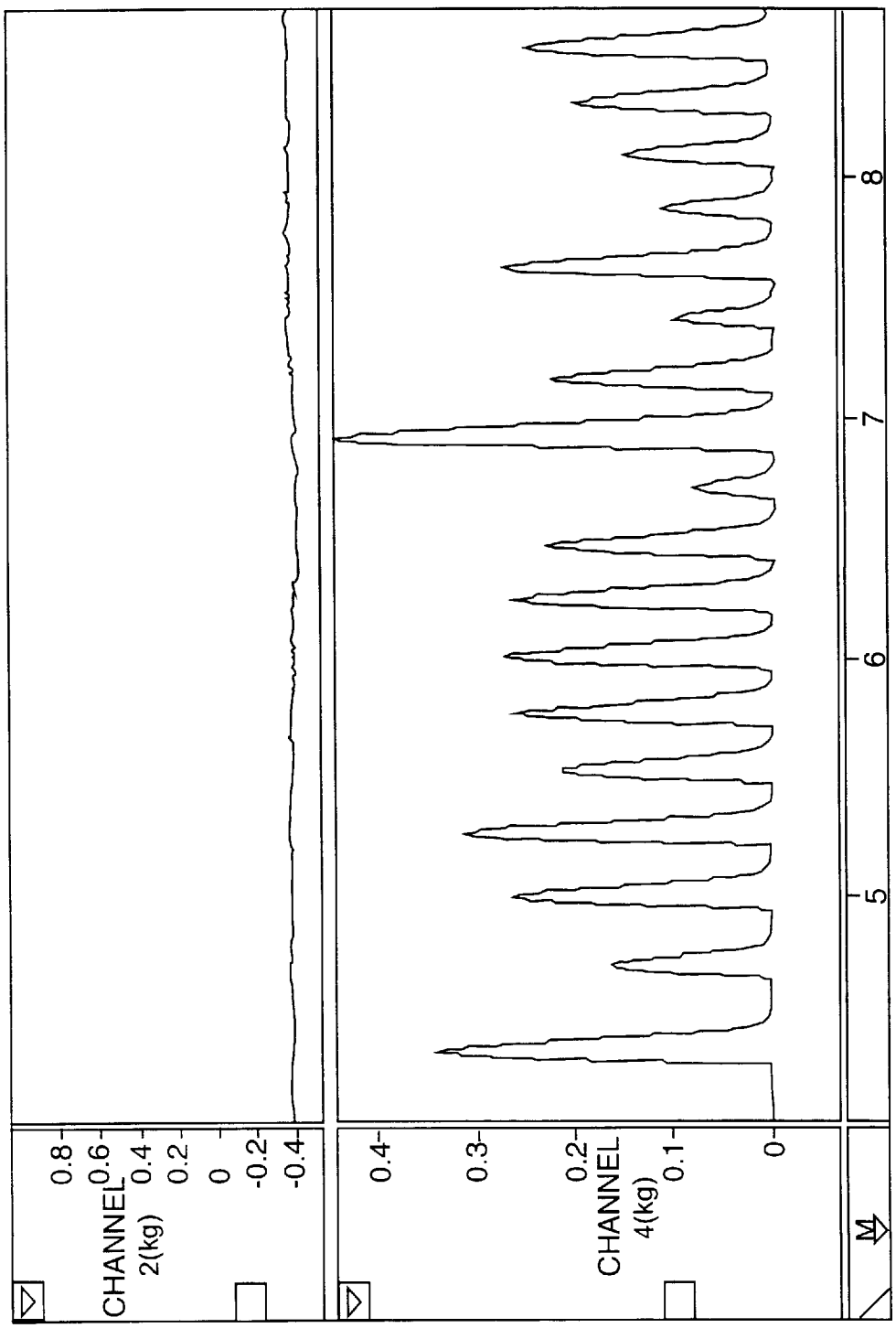

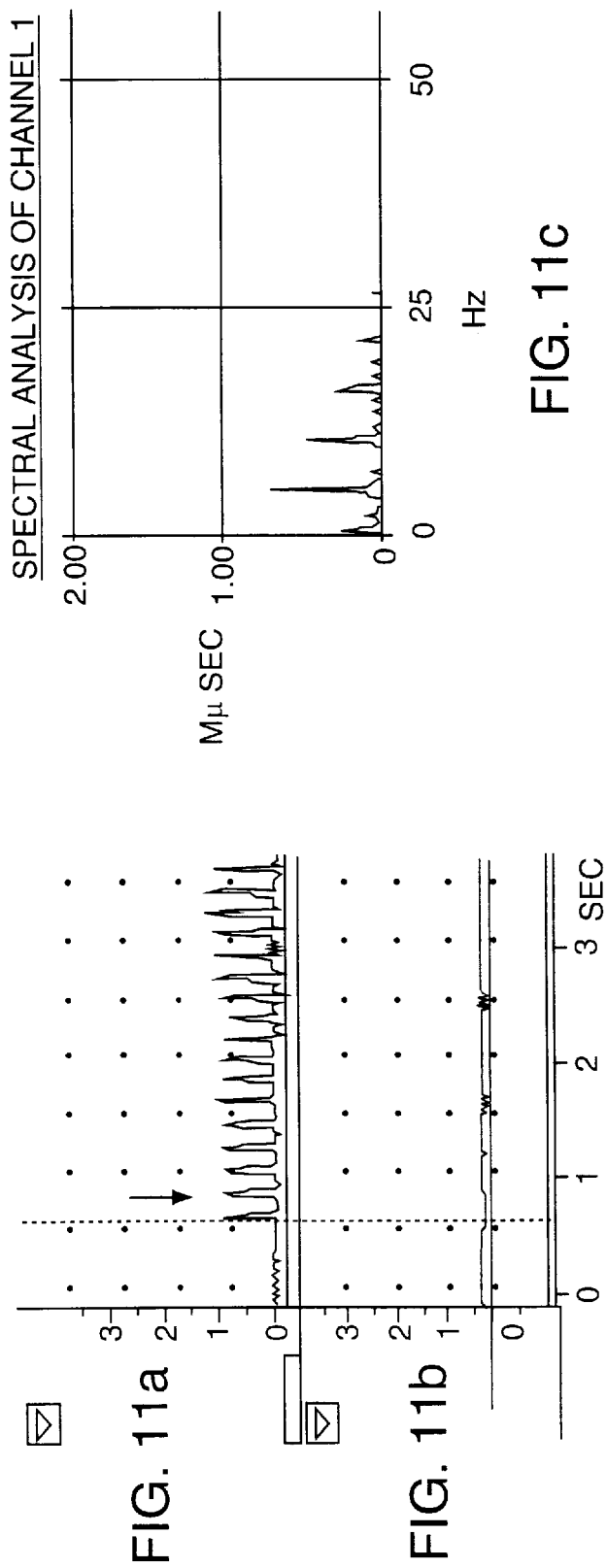

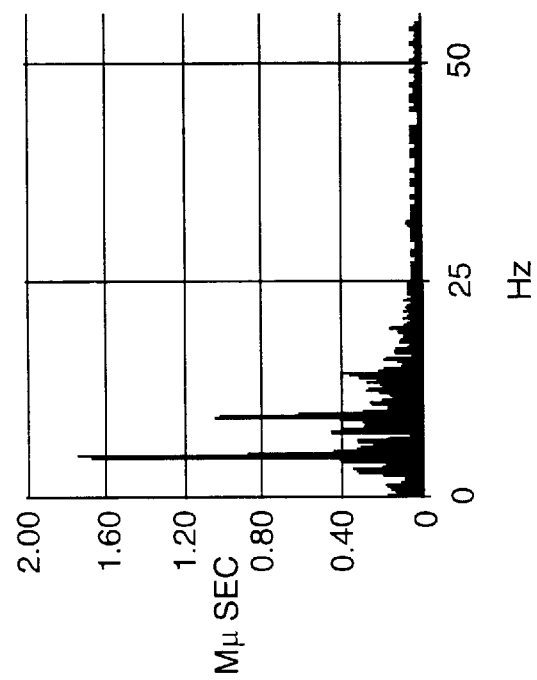
FIG. 12c
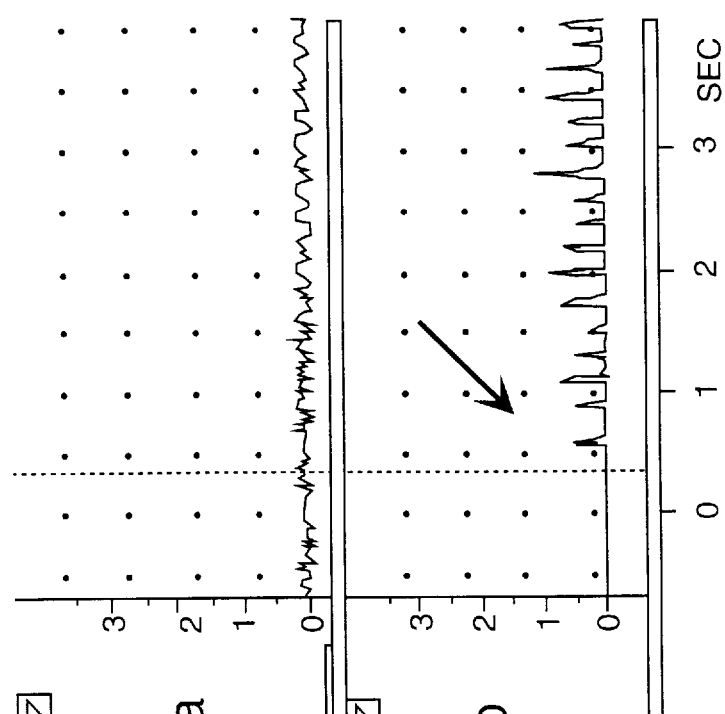
FIG. 12a
FIG. 12b

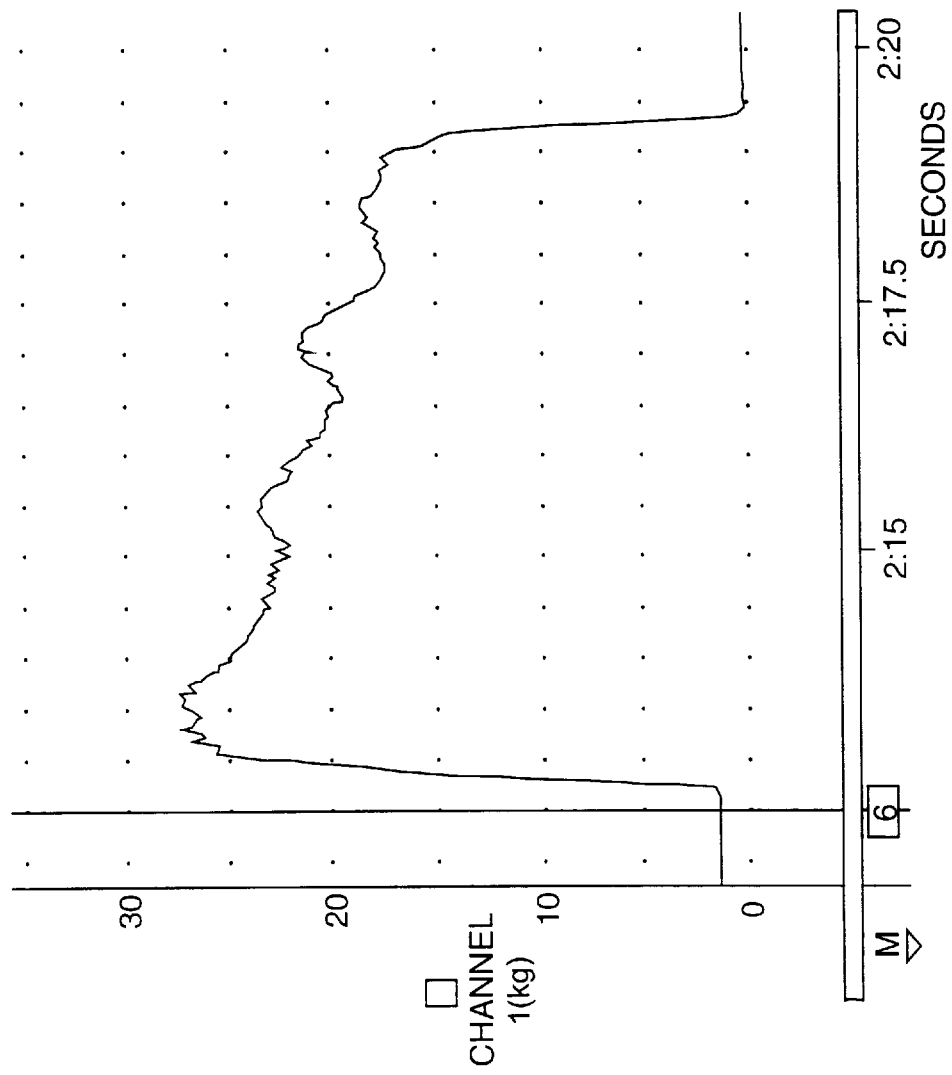

DIGITAL MOTOR EVENT RECORDING SYSTEM

BACKGROUND OF THE INVENTION

The invention relates to biomedical devices for quantitative measurement and analysis of progressive loss or recovery of motor activity in human subjects.

Diseases such as stroke, amyotrophic lateral sclerosis (ALS), and Parkinson's disease frequently result in motor deficit. It would be useful for medical personnel attending to victims of these diseases to have available a straightforward and quantitative measurement of the extent of motor deficit. Such a test would, for example, allow assessment of stroke severity, which would in turn assist in the development of standardized protocols for treatment keyed to severity. Furthermore, ongoing research toward the development of palliative drugs necessitates accurate assessment of the progress achieved by these drugs. Several methods have been developed for these measurements.

Following stroke, subjective criteria are frequently used in the measurement of motor function. In one such test, a subject curls his or her fingers and attempts to resist an examiner's attempt to straighten them. Inability by the examiner to uncurl the fingers is scored as 5+ on the Medical Research Council's 0 to 5+ scale; mild weakness is 4+, action against gravity but no other external force is 3+, and so forth down to 0, equaling no resistance from the subject. However, such studies have been shown to be irreproducible and the results are often ambiguous.

Other tests, including evaluations of grip strength and finger tapping ability, provide more useful measurements in the assessment of stroke severity. For example, a spring-based dynamometer with a mechanical needle gauge can be used to measure the force with which the subject can squeeze (Spreen et al. "A Compendium of Neuropsychological Tests", 1991, pp. 367–373; Trombly *Occupational Therapy for Physical Dysfunction*, 1995, p. 151; Kellor et al. *Am. J. Occup. Ther.*, 1971, Vol. XXV, No. 2, pp. 77–83; Heller et al. *J. Neurol., Neurosurg., and Psych.*, 1987, Vol. 50, pp. 714–719). Electrical dynamometers have also been developed with the capability of recording maximal grip strength (contraction amplitude) or the time between the initiation of contraction and the peak contraction amplitude (contraction time).

Finger tapping ability has been tested with devices ranging from mechanical tallying units (Heller et al. *J. Neurol., Neurosurg., and Psych.*, 1987, Vol. 50, pp. 714–719; Spreen et al. "A Compendium of Neuropsychological Tests", 1991, pp. 367–373) to video surveillance systems that capture minute finger tremors (Frischer *Neuropsychologia*, 1989, Vol. 27, No. 10, pp. 1261–1266). Still other devices include electrical counters capable of calculating tapping frequency and interval between taps, and the mean, standard deviation, and coefficient of variation for these quantities (Shimoyama et al. *Arch. Neurol.*, 1990, Vol. 47, pp. 681–684).

Two scales are widely used in the evaluation of neurological status following stroke. The NIH stroke scale includes numerous components, such as assessment of language ability, vision, sensory function, level of consciousness, and motor function. The Fugl-Meyer scale assesses sensory motor function after stroke. A Fugl-Meyer arm motor subscore can also be employed; this subscore examines a multitude of factors, including deep tendon reflexes, synkinesia, strength, dexterity, tremor, and coordination.

Assessment by these traditional methods (i.e., NIH or Fugl-Meyer) is burdened by several considerations. First, excellent interobserver agreement is achieved only with extensive training. Second, the tests are time consuming, requiring about 15 minutes or longer per test for an experienced analyst. These two issues have increased in importance in recent years due to the proliferation of new drug trials.

SUMMARY OF THE INVENTION

The invention is based on the discovery that data generated by a manually activated transducer electrically connected to a computer can be processed in a manner that provides an objective and reproducible determination of recovery or degeneration of a subject's motor abilities. The computer receives, stores, and processes the signal transmitted by the transducer. This system can measure parameters such as force, integral of force production over the duration of the motor event, rates of onset and decay of force production, and frequency of repetitive motor events; and statistical moments pertaining to these parameters, such as maximum value, mean, standard deviation, and coefficient of variation.

The data obtained with the system can be used, for example, in diagnosing the severity of a motor deficit. Through experimentation with the device, for instance, it has been found that the integral of force production shows a strong correlation with stroke severity. Other applications include the assessment of the efficacy of various drugs used to treat motor deficits or the study of patterns of degeneration caused by various diseases.

In general, the invention features an apparatus for measuring a set of repetitive, individual motor events of a subject (e.g., a human subject), where the motor events have a frequency and force component. The apparatus includes a transducer, adapted to generate an analog signal corresponding to frequency and force of the subject's repetitive motion; an amplifier, which amplifies the analog signal; an analog-to-digital (A/D) converter, which converts the analog signal into a digital signal; and a computer. The transducer, amplifier, A/D converter, and computer are connected, in that order, via electrical cables. The computer is programmed to receive the digital signal as input, store the digital signal for subsequent retrieval, retrieve the stored digital signal for processing, and process the stored digital signal. The processing includes the measurement of mean force amongst the set of individual motor events over time and measurement of the mean frequency of the set of individual motor events over time.

The transducer can be adapted to generate an analog signal when the subject taps the transducer with a finger or squeezes the transducer with a hand.

The processing can also include (1) the measurement of the integral of the force of the individual motor events over a predetermined time interval, (2) the measurement of the coefficient of variation of the force amongst the set of individual motor events, (3) the measurement of the coefficient of variation of the frequency amongst the set of individual motor events, (4) the measurement of the maximum force amongst the set of individual motor events, or (5) the measurement of the duration of individual motor events.

In certain embodiments, the apparatus includes a second transducer, also electrically connected to the computer (i.e., via an amplifier and A/D converter). The second transducer is adapted to generate a second analog signal corresponding to frequency and force of a second repetitive motor event of the human subject. The first and second signals can be obtained simultaneously or at different times. The processing can also include the calculation of the ratio of the force and frequency determined by processing the first signal to the force and frequency determined by processing the second signal. For example, it could be desirable to calculate the strength of the left hand as a percentage of the strength of the right hand. As another example, it can be useful to know whether or not the right hand involuntarily squeezes when a finger of the left hand is tapping.

The transducer can be mounted within a frame. The frame includes an armrest which allows the subject's arm to be positioned in the same location for each finger tap, at least one retaining strap connected to the armrest to prevent movement of the subject's arm during finger tapping and to isolate movement to the finger, and a slot which holds a base of the transducer in place. The slot is located adjacent to the armrest so as to allow the subject's finger to contact the transducer (e.g., the finger taps at the center of the transducer's actuator in order to ensure maximum transmission of the finger's force).

Another embodiment of the invention features an apparatus for measuring a force produced by a single motor event of a subject (e.g., a human subject) over an extended period of time. The period of time may be a tenth of a second, one second, five seconds, a minute, or more. The apparatus includes a transducer, adapted to generate an analog signal when the subject produces a sustained force over an extended period of time; an amplifier, which amplifies the analog signal; an A/D converter, which converts the analog signal into a digital signal; and a computer. The transducer, amplifier, A/D converter, and computer are connected, in that order, via electrical cables. The computer is programmed to receive the digital signal as input, store the digital signal for subsequent retrieval, retrieve the stored digital signal for processing, and process the stored digital signal. The processing includes the measurement of the force at multiple time points during the extended period of time and calculating the integral of the force produced over the duration of the motor event, e.g., over the extended period of time.

The transducer can be adapted to generate an analog signal when a subject performs a sustained squeeze with a hand.

There can be a second transducer included, also connected to the computer electrically (e.g., via an amplifier and A/D converter). The second transducer is adapted to generate a second analog signal when the subject produces a second force over an extended period of time. The first and second signals can be obtained simultaneously or at different times. The processing can also include calculation of maximum force, time course, and an integral of force with respect to time, for each signal, over the duration of the motor event.

It is sometimes desirable for the processing to include a calculation of the ratio of the force determined by processing the first signal to the force determined by processing the second signal. If the first and second signals are obtained simultaneously, this ratio can be indicative of the extent of mirror movement. A mirror movement is an unintentional motor event complementary to an intentional contralateral movement. For example, when a stroke patient attempts to squeeze with his or her paretic hand, the good hand also tends to squeeze, albeit to a lesser extent. If the first and second signals are obtained at different times, the ratio can provide normalized values. For example, the grip strength of one hand can be expressed as a percentage of the grip strength of the other hand. Since normally this ratio is around one, a lower value provides a measure of motor function deficiency in one hand.

The apparatus can also include a plurality of electromyography leads or other input devices, electrically connected to the computer. The input devices are able to detect temperature, blood pressure, sound, or range of motion, for example.

In another embodiment, the invention features a method of analyzing a motor event of a subject (e.g., a human subject). This method includes (1) obtaining at intervals of time an analog signal proportional to the intensity of the subject's exertion of force on a transducer; (2) amplifying the analog signal to make an amplified analog signal; (3) converting the amplified analog signal to a digital signal; and (4) processing the digital signal. The processing includes analyzing the waveform of said signal to obtain frequency and amplitude data.

The transducer or transducers can be placed within an MRI instrument so that the subject can actuate the transducers during the course of an MRI session.

Electromyography lead signals can also be processed (i.e., with a plurality of electromyography leads electrically connected to said computer). Furthermore, the processing can include comparing the timing of signals generated by the transducers and signals generated by the electromyography leads. This method can provide evidence of latency of movement compared with the action of the muscle cells.

The method can also include the simultaneous monitoring of contralateral motor events with the aid of a second transducer electrically attached to the computer. In this case, the method can also include dividing parameters or moments pertaining to activity of a body part (e.g., a hand or a finger or a group of fingers) with abnormality of movement by the corresponding parameters or moments pertaining to activity of the contralateral body part without abnormality of movement. This can yield normalized data.

The method can also include the isolation of a given joint movement with the aid of a retaining strap.

In another embodiment, the invention features a method of analyzing a motor event of a subject over an extended period of time. The method includes (1) obtaining at intervals of time an analog signal proportional to the intensity of said subject's exertion of force on a transducer; (2) amplifying the analog signal to make an amplified analog signal; (3) converting the amplified analog signal to a digital signal; and (4) processing said digital signal. The processing includes measuring the force at multiple time points during the extended period of time, and calculating an integral of force over the time period.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

An advantage of the new systems and methods is the ability to capture the entire waveform of a motor activity, not just a record of the occurrence of that activity. This is possible because the system samples and records over one hundred data points each second, allowing, for example, the calculation of the integral of force production over time or analysis of the symmetry of force production and decay curves. Both of these measurements have been found to be useful in the assessment of stroke severity.

Whereas evaluation with traditional scales, such as NIH stroke scale or Fugl-Meyer scale, is time-consuming (i.e., about 15 minutes per test) and requires extensive training for dependable interpretation of results, the devices and methods disclosed herein provide a rapid and facile assessment which reliably correlates with the traditional scales.

Other features and advantages of the invention will be apparent from the following detailed description, and from the claims.

BRIEF DESCRIPTION OF THE DRAWINGS

FIGS. 7A and 7B are plots of the record of a stroke patient's squeezing a transducer in the good hand (7A) and corresponding mirror movements recorded simultaneously with a transducer in the paretic hand (7B).

FIGS. 9A and 9B are plots of the record of a stroke patient's index finger tapping a transducer with the good hand (9B) and corresponding mirror movements recorded simultaneously with a transducer in the palm of the paretic hand (9A).

FIGS. 11A to 11C are plots of the record of a stroke patient's tapping a transducer with all fingers of the good hand except the thumb (11A), and the corresponding mirror movements recorded simultaneously with a transducer in the palm of the paretic hand (11B). Both raw data (11A and 11B) and Fourier transformed data (11C) are provided.

FIGS. 12A to 12C are plots of the record of a stroke patient's tapping a transducer with all fingers of the paretic hand except the thumb (12B), and the corresponding mirror movements recorded simultaneously with a transducer in the palm of the good hand (12A). Both raw data (12A and 12B) and Fourier transformed data (12C) are provided.

FIGS. 16A and 16B are plots of the record of a stroke patient's squeezing a transducer with paretic (16A) and good (16B) hands (separately, not simultaneously), six days post-stroke.

DETAILED DESCRIPTION

The invention uses a manually activated transducer electrically connected to a computer to generate digital data, and a computer program to process the digital data in a way that provides an objective and reproducible determination of recovery or degeneration of a subject's motor abilities. The computer captures, displays, stores, and processes the signal transmitted by the transducer. This system allows measurement of variables such as muscle strength, integral of force production over the duration of exertion, frequency of serial exertions, and decay of force production over time. The data obtained with the system can be used both in diagnosis and in treatment.

The invention can be implemented in hardware or software, or a combination of both. The data processing method can be implemented in computer programs executing on programmable computers each comprising a processor, a data storage system (including memory and/or storage elements), at least one input device, such as an A/D converter, and at least one output device, such as a CRT or printer. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language. In general, individual programs described herein are available commercially.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Digital Motor Event Data Generating and Recording System

Figure 1:
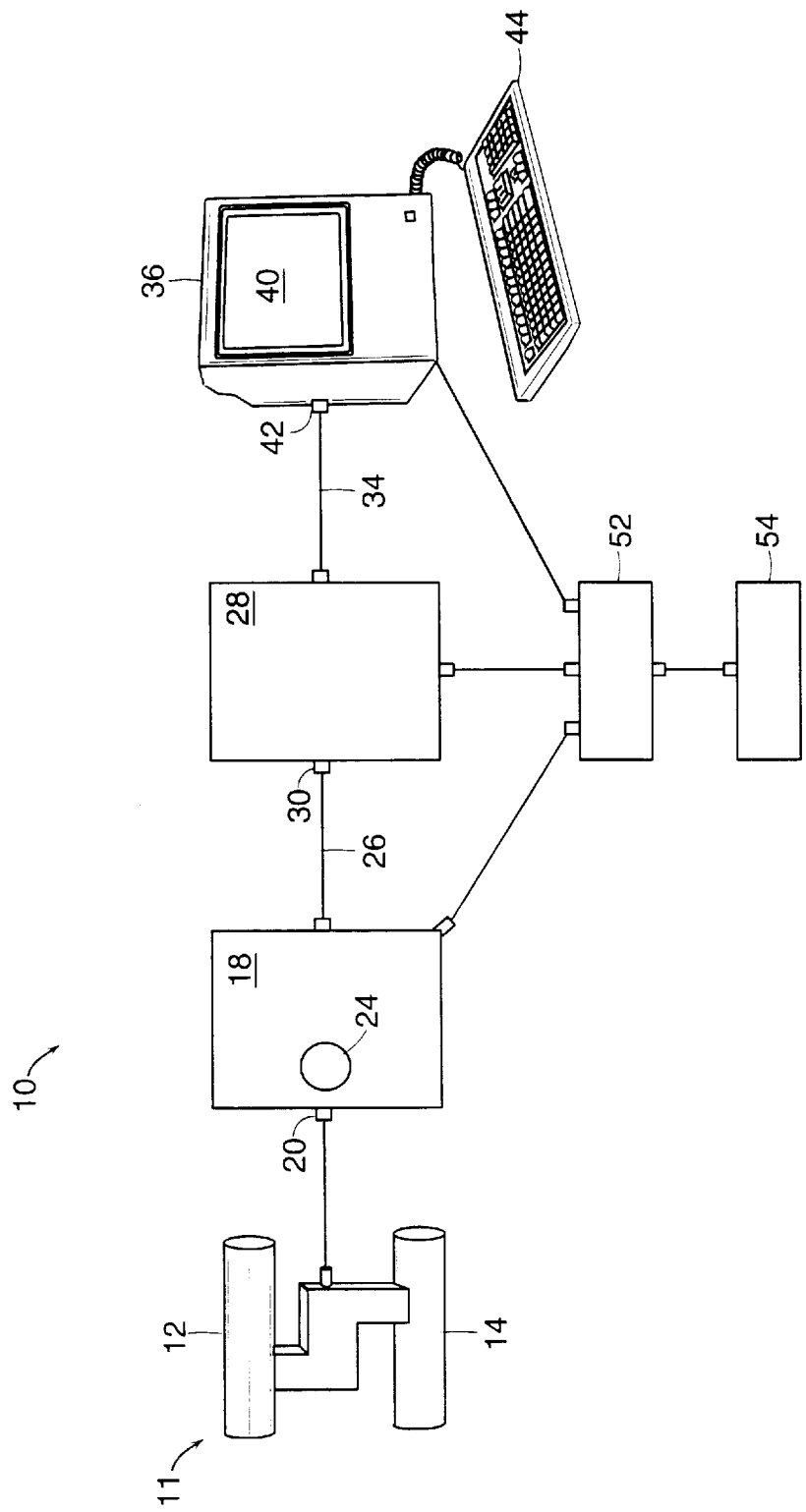
FIG. 1 is a schematic of a digital motor event recording system with a detailed view of the transducer.

As shown in FIG. 1, the system 10 includes a transducer 11, an amplifier 18, an A/D converter 28, and a computer 36, including a specific computer program. The transducer 11 must have an appropriate size and shape to be actuated by a subject's squeezing or tapping. The transducers used in the studies described herein were obtained from Interface (Scottsdale, Ariz.), although other transducers can also be used. The Interface SSM-AJ-250 (250 lb. maximum force) was used for squeezing analysis. The Interface SSM-AJ-50 (0–50 lb. range) was better suited for tapping analysis or for detection of mirror movements during squeezing analysis, as it is more sensitive. The transducer converts the hand's mechanical force into an electrical signal.

The transducer 11 is connected electrically to an amplifier 18, which increases the signal and supplies power for transduction, if necessary. Nearly any amplifier of suitable power limitations can be used; the ETH-200 amplifier (AD Instruments, Milford, Mass.) was chosen for the present applications. The transducer output is fed into the amplifier via a standard eight pin DIN plug 20.

The amplifier 18 then feeds the signal via BNC cable 26 to an A/D converter 28. The A/D converter can be custom made or can be purchased. Examples of acceptable commercially available A/D converters include MacLab (AD Instruments), or converters from National Instruments or Kiethly-Metrabyte. The amplifier feeds into the (+) channel 30 as a single line, or, if the signal-to-noise ratio is found to be unacceptably high (e.g., as a result of electromagnetic interference), into a differential plug into both (+) and (−) channels. The A/D converter 28 communicates with a computer 36, e.g., a personal computer such as a Macintosh 540c, via an SCSI wire 34. The computer 36 includes software which allows, for example, storage, analysis, and excerpting of the digital data.

Figure 4:
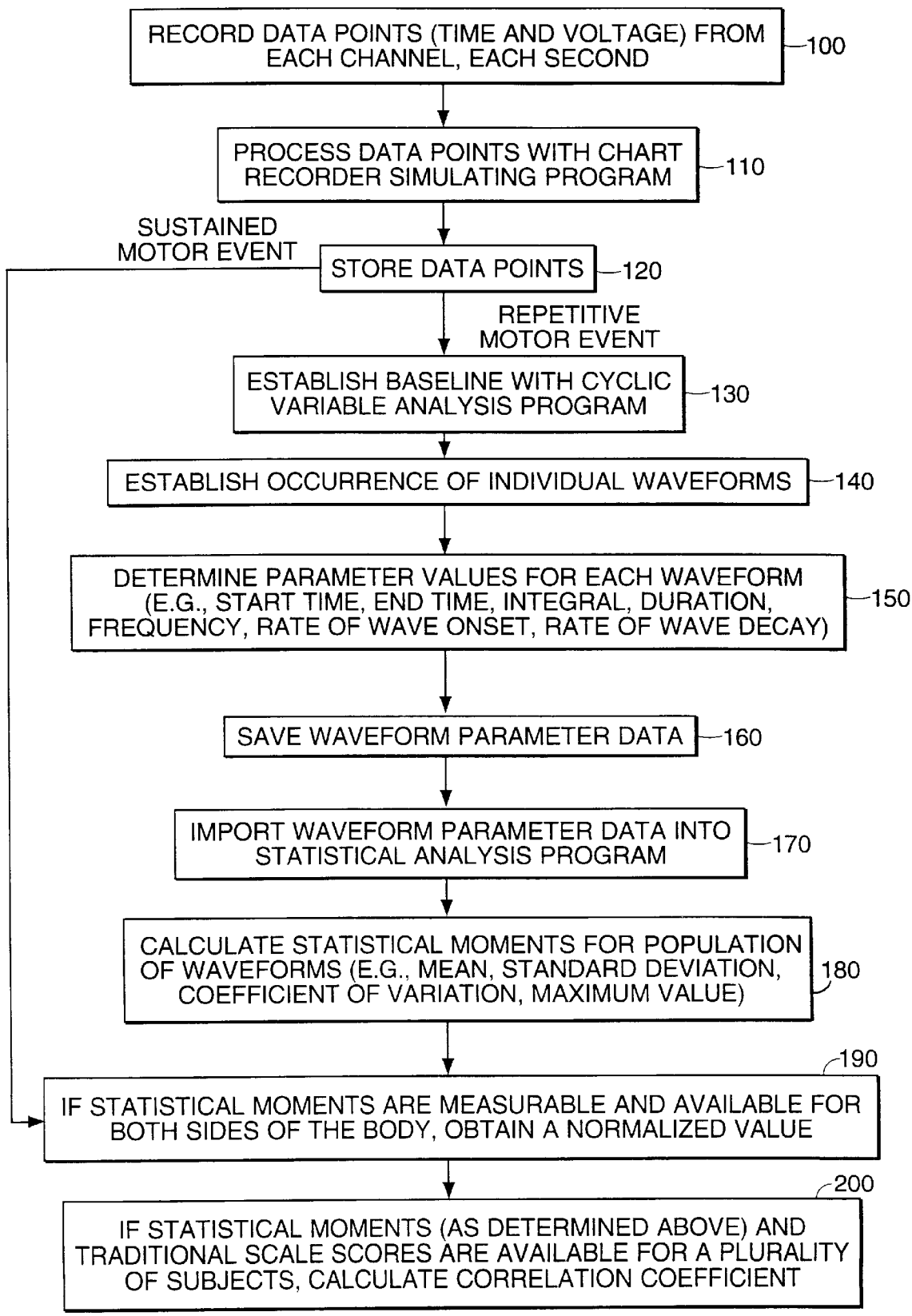
FIG. 4 is a detailed flow chart of all the steps in the method performed by the computer.

The steps carried out by the computer 36 are shown in the flow chart in FIG. 4. For each record, the computer records a number of digital data points for each channel of input equal to the sampling rate (i.e., data points per second) multiplied by the duration (in seconds) (step 100). The time of each data point and the amplitude (i.e., voltage) of the digital signal at that time are recorded by a chart recorder simulating program (step 110). The data points can be stored in a file (step 120) and displayed graphically on the computer monitor 40 or printed on paper. Chart recorder simulating programs are well-suited for creating these files. These programs can be custom written, although there are numerous commercially available software packages available, such as Chart (AD Instruments), Labview (National Instruments), Matlab (Mathworks, Natick, Mass.), or Brainwave (Datawave), that are suitable. The file can be stored in the memory of the computer, or floppy disks, on a CD, or other storage medium.

To analyze data concerning repetitive activities, such as finger tapping, it is helpful to use a program that establishes the occurrence of individual waveforms from the cyclic event (step 140). The program does this by establishing a baseline (step 130). Each wave should cross the baseline twice, once on the onset and once on the decay. Once the waves are defined, the values of various parameters can be determined (step 150). The relevant parameters generally include start time and end time for the wave, as well as the integral of the wave, the rate of wave onset, the rate of decay, the duration of the wave ([end time]−[start time]), and the frequency (1/[[start time]−[start time of previous wave]]) for the wave. Programs to carry out these functions are easily written; alternatively, many chart recorder simulating software packages include cyclic variable analysis modules (see examples above) that can be used herein.

For analysis of the population of waves, the results of cyclic variable analysis are exported, for example in text format, to a statistical analysis program. Generally the data is arranged as a table in the text file such that each wave will have a separate row in the text file, and each parameter has a column (step 160). The statistical analysis program reads this data file (step 170) and calculates statistical moments from it (step 180) (e.g., mean, standard deviation, coefficient of variation, or maximum value). Statistical analysis programs can be custom programmed to suit individual needs, or can be obtained commercially. Examples of commercially available statistical analysis software packages include STATVIEW® (Abacus Concepts Inc., Berkeley, Calif.), JMP®, JMP-IN edition (SAS Institute, Cary, N.C.), or Statworks (Cricket Software, Phila., Pa.).

For convenience, the computer, amplifier, and A/D converter can all be plugged into a single multi-plug extension outlet 52, connected to a transformer 54, such as a Stancor GIS 150 (150 VA/SEG 115 V) isolation transformer. The transformer 54 prevents electrical injury to the user and to the subject; nevertheless, the system is not recommended for use with subjects who have open flesh or external catheters which enter into deep cavities. The entire system can be mounted onto a cart on wheels.

For reproducible analysis of tapping, it is often desirable to isolate the muscles responsible for the movement of the index finger. This can be achieved by mounting the transducer within a specially designed frame as shown in FIGS. 2 and 3.

Figure 2:
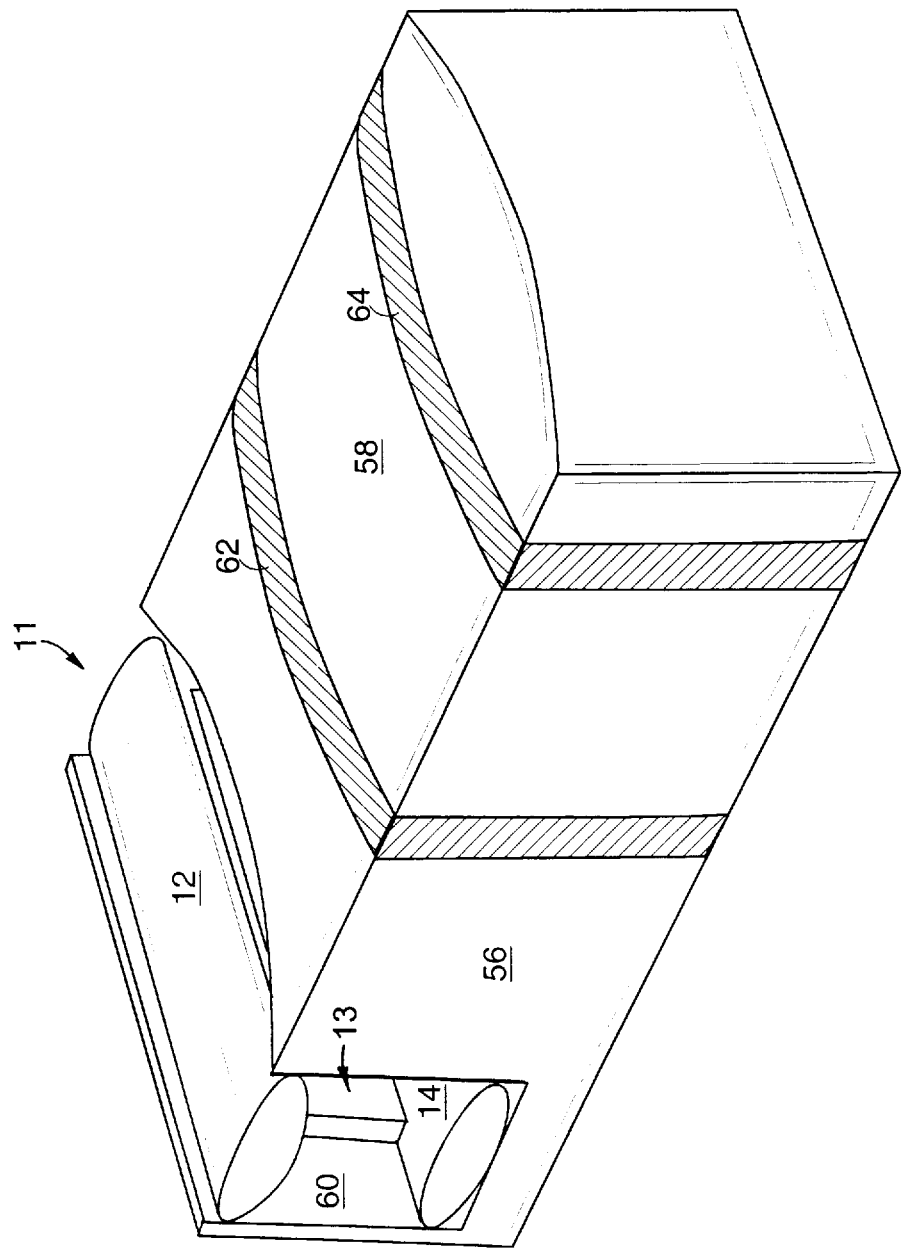
FIG. 2 is a three-dimensional schematic view of a restraining-box armrest for finger tapping analysis.

As shown in FIG. 2, one frame design has a box-like structure 56. The frame has at least one restraining strap 62 for the wrist, and optionally, a second strap 64 for the forearm. These straps prevent movement of any muscles other than those required for tapping of the index fingers. The frame can have a concavity 58 to fit and position the arm. The frame should also have a slot 60 designed to hold the transducer 11 in such a manner as to prevent movement of the base 14 of the transducer, while leaving the actuator 12 of the transducer exposed and positioned for maximum, unrestricted contact with the tip of the index finger when the wrist and arm are strapped to the frame.

Figure 3:
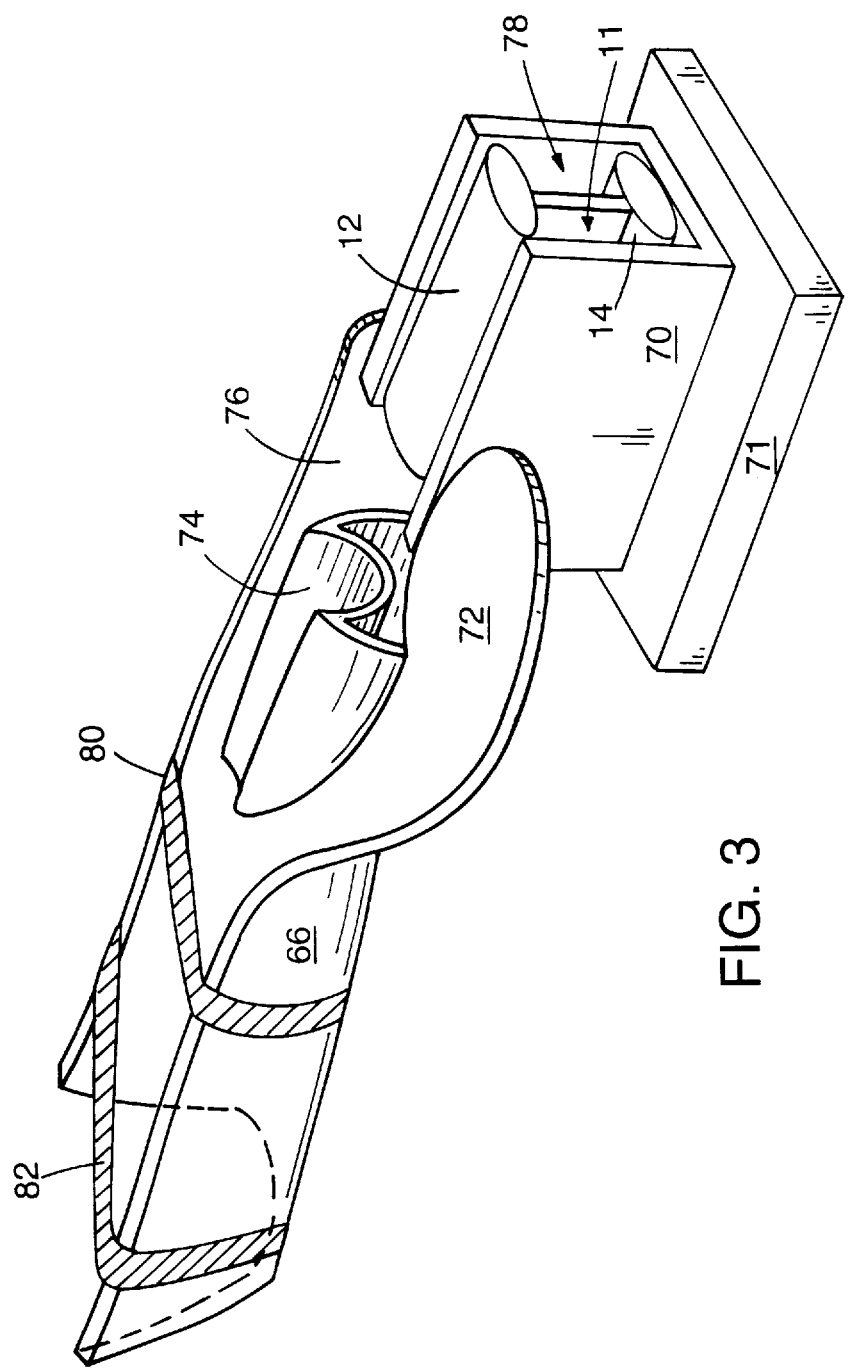
FIG. 3 is a three-dimensional schematic view of a molded armrest for the finger tapping analysis.

FIG. 3 shows an alternative frame design that includes a concave, arm-fitting armrest 66, e.g., of plaster or hard plastic, rigidly secured to a holder 70. The armrest has a thumb guide 72 for positioning the thumb on one side of the armrest 66, an index finger guide 74, located above the actuator of the transducer 11, and a finger guide 76, to cradle the remaining three fingers on the side opposite the thumb. The armrest shown in FIG. 3 is designed for the left hand, but an equivalent armrest can be made for the right hand.

A restraining strap 80 holds the wrist in place. A second, optional restraining strap 82 can be used to hold the forearm in place. Holder 70 has a slot 78, designed to hold the transducer 11 in such a manner as to prevent movement of the transducer base 14, while leaving the transducer actuator 12 exposed and positioned for maximum, unrestricted contact with the tip of the index finger when the arm is strapped to the frame. Holder 70 rests on platform 71, which is shown in FIG. 3 as extending only slightly beyond holder 70. However, platform 71 can be extended to the end of armrest 66, and be used to provide support for armrest 66, which can then be secured to both platform 71 and holder 70.

The system described above produces a permanent digital record of a neurological behavior. Detailed processing and analysis of the digital data can be performed either at the time of measurement or at a later time. Below are descriptions of data acquisition and data analysis.

Methods for Obtaining Data

The A/D converter (e.g., MacLab) and its amplifiers are turned on. Next the A/D converter is connected to the computer (e.g., Macintosh), for example via a SCSI connection. The A/D converter should be equipped with a SCSI output line that terminates in a male SCSI connector, and the computer should be equipped with a SCSI port (female connector) 42. Other connections can also be used. The computer is then turned on and the strip chart simulating software program is started. Ideally, the program should allow preset templates to be created and saved for particular applications. For example, a template for finger tapping should set sensitivity parameters appropriate for the voltage likely to be generated by the force of a finger tapping on a transducer. The template can also establish the sampling rate for data recording. A template increases the efficiency of testing, since it obviates the need for resetting all of the parameters each time the computer is turned on.

Before using the system to analyze subjects, the system must be zeroed and calibrated. First, the transducer is placed horizontally on a table surface, such that zero gravitational force is exerted. The recording begins after clicking on a "START" button, e.g., using a "mouse." Each amplifier has a knob 24 used to adjust the zero point. At this time, a recording is made while the amplifier knob is rotated to bring the baseline being traced on the screen to zero. Next, a 2 kg weight is suspended from each transducer, confirming the calibration. A 100 gram weight is suspended, again to confirm the calibration. To date, maintenance of calibration by this setup has consistently been confirmed.

It should be noted that in the examples and figures below, forces are reported with units of kilograms, where the conventional units of force are pounds or newtons. Kilograms are used merely because of the calibration with weights having a known mass. Thus, what is referred to herein as force is actually the mass exerting an equivalent force in the gravitational field of the earth.

The subject who is to be examined is then positioned. The subject is seated comfortably, either on the edge of a bed or in a chair without arms. The subject's arms are placed onto a table, such that the elbow is flexed at approximately 90 degrees and the wrist is straight. The right and left hands can be tested in any order, but the examiner should be consistent with each subject to ensure maximal reproducibility.

Preferably, there are two transducers: one is gripped by the hand being tested, while the other is held in the hand at rest. The purpose of having a second transducer in the resting hand is to record mirror movements, defined as unintentional movements in a body part occurring during voluntary movement of the contralateral body part. These movements are seen in normal children and in disease-affected adults, and they are common, although usually transiently, during the weeks of recovery that follow a stroke. By placing a second transducer in the resting hand, and not explaining to the subject the purpose of this transducer, the mirror movements which occur inadvertently during performance of the motor task can be monitored.

The subject is given a standard set of instructions, such as: "With your right hand, I want you to squeeze as hard as you can until I tell you to stop. Let's try a sample squeeze. That's good. O.K., when I say go, remember to squeeze as you've just done, as hard as you can, until I say stop."

The tasks investigated have been of a 5 or 10 second duration, and include (1) sustained squeezing, (2) rapid, hard squeezing, (3) maximally rapid tapping of index finger (where a minimum force of 50 gram is required), (4) maximally rapid tapping of 4 fingers (all except thumb) simultaneously, (5) index finger tap to a 2 Hz metronome, and (6) 4 finger tap to a 2 Hz metronome. In addition, recording of index finger tapping for 3 minutes has also been done.

Each task can be annotated in the recording by typing a brief description on the computer keyboard 44 prior to task performance. The "START" and "STOP" commands are noted in the record as well. Typically, the recording is halted between tasks. The purpose of the notations is twofold: (1) to record the nature of the instructions at the time of data acquisition, and (2) to indicate the precise timing of the command. The latter is indicated by the software by producing a line across the data recording representing the moment of notation inscription. When digital data acquisition is complete, the recording of the data is stored on a diskette or other storage medium.

Methods for Statistical Analysis of Stored Data

It is important that software configurations are used consistently for data acquisition and extraction, both for comparisons between subjects and for multiple tests of a single subject. As the subject performs a motor task, the signal is transduced, amplified, digitized, and sent to the computer. The signal is displayed and recorded using a strip chart simulating program.

For the examples provided below, a template was created to include acquisition of 100 data points/second, although other sampling rates can be used instead. As mentioned above, the force exerted by the subject is reported in the examples as mass in kilograms. The actual force (in Newtons) can be obtained by multiplying the mass by 9.8 m/sec$^2$ (the gravitational constant on Earth).

Because the digital data can be stored permanently, it is possible and often desirable for efficiency to perform statistical analysis off-line. As described above, more detailed data analysis can be performed when the features of a tracing are captured using cyclic variable analysis. A cycle is a waveform corresponding to each individual squeeze or tap. Each of the tapping or squeezing waveforms will cross a properly set baseline twice, once on its onset, and again on its decay. Cyclic variable analysis yields data relating to: (1) the time of the wave, (2) the frequency (in Hertz, calculated with respect to the time interval since the wave immediately preceding), and (3) the force (the amplitude of the wave's peak, in kilograms).

One text file can contain all of the waveforms collected during ten seconds of index finger tapping. This is often 40 to 50 waves. For the population of waves, statistical moments are determined for each parameter. These moments include mean, maximum value, standard deviation, percentiles, and coefficient of variation. Examples of relevant parameters include frequency, duration, time of occurrence, integral, and rates of onset and decay. As described below, some of these parameters, and the statistical moments relating to them, provide information which correlates well with traditional scales for the assessment of subjects with varying motor function ability.

Use of the Digital Motor Event Recording System

The digital motor event recording system has enabled calculations pertaining to motor behavior tracing which have not been previously described. Thus, review of the data of Example 1, below, reveals that there is a highly significant correlation between stroke recovery status, as measured by Fugl-Meyer and NIH scales, and certain squeezing parameters. More specifically, these parameters include performance of the stroke-affected hand, normalized for each individual by dividing by the unaffected hand performance (step 190), in: (a) the maximum force, (b) the integral over five seconds of squeezing, (c) the time for maximum force generation, and (d) the ratio of force at five seconds to maximum force. A highly significant correlation was discovered between recovery status and (a) peak strength or (b) the integral over five seconds, but little or no significance for (c) time to peak force or for (d) ratio of force at five seconds to maximum force. Given the statistical moments of step 190, and data corresponding to traditional scale (i.e., NIH) evaluations, the program can evaluate correlations between the two (step 200). The conclusion is that force produced during squeezing relates to stroke recovery irrespective of how long it took to generate the force and for how long the force was sustained.

At a time after stroke when clinical examination and standard scales of stroke recovery show little or no deficit, the coefficient of variation for tapping frequency, as determined through statistical analysis of the data obtained with the digital motor event recording system, in a subject recovering from stroke can still be twice that found in normal, age-matched controls, because these methods permit a objective, quantitative, and sensitive analysis of fine aspects of task performance.

For some experiments, it is desirable to place the transducer in the high magnetic fields used in a functional MRI experiment. For example, a quantitative statistical analysis of motor behavior has been performed with the device along with the corresponding brain activation images produced concurrently using functional MRI technology. These images depict the brain regions activated in the production of the motor behavior. Accurate measurement of fine details of motor behavior, correlated with brain activity should lead to a more precise understanding of the connection between brain and motor function. Because space is often limited within the MRI device, it is desirable to use the smallest frame available for finger tapping tests; generally, this is the molded frame rather than the restraining-box frame. Also, because metal objects (such as the amplifier or the A/D converter) cannot be placed near the MRI's powerful magnet, a longer cord must be used for connecting the transducer to the remainder of the apparatus.

While the possibility of using two transducers, one in each hand, has already been discussed, in some cases it is useful to have additional transducers connected. For instance, four transducers can be used as follows: a transducer in each hand and electromyography (EMG) leads on each arm to record the electrical signals generated by muscle activity. Another possibility is to measure tapping, for example, in combination with squeezing, EMG, or other domains of input. For arthritis patients, a measure of the number of degrees of joint movement, as well as the force generated across the joint, would be of interest. For aphasia patients after stroke or head injury, a recording of the subject's voice (speech output end of aphasia) simultaneous with a record of word recognition performance (speech input end of aphasia) would be suitable. For disability claims, simultaneous recording of a motor behavior (squeezing in carpal tunnel syndrome or leg lifting in low back pain) with the subject's comments on pain (at what point pain occurs, when it becomes unbearable) would be desirable.

Neurologists perform tests, such as lifting each leg slowly, to assess when the low back is stressed and therefore what the likelihood of certain neurological conditions is, but there is much guesswork and approximation. With a digital device, a permanent record can be obtained, showing precise temporal coupling of a motor behavior and a subject's response to that behavior.

The following are examples of the use of the system.

EXAMPLE 1

Correlation of Motor Performance (as measured with the digital motor event recording system) With Traditional Scales Twenty four subjects were studied. In each subject, two standard scales of neurologic function were measured (the Fugl-Meyer arm motor score and the NIH stroke scale), along with assessments of squeezing and tapping from both hands using the digital motor event recording system. Test subjects had all had a stroke producing motor system abnormalities, but no limiting deficits in attention, language, or level of consciousness. The Fugl-Meyer arm motor score (the Fugl-Meyer motor score is broken down into arm, leg, motor, and sensory sections), a hand subsection of the Fugl-Meyer arm motor score, and the NIH stroke scale each showed a highly significant correlation with data yielded by the digital motor event recording system.

Strength and tapping speed were found to vary widely among control subjects (i.e. subjects who had never had a stroke) in this study, in agreement with previous reports in the medical literature. Test performance appeared to be influenced by multiple factors including age, level of education, and gender. To account for this variation, each test subject's paretic (Par) hand performance was divided by the "good" (G) (i.e., nonparetic) hand performance to obtain a normalized score (Par/G).

The abilities measured included fast squeezing, wherein subjects were asked to squeeze as hard as possible, as quickly as possible; sustained squeezing, wherein subjects were asked to hold the strongest grip for a minimum of five seconds; and index finger tapping, wherein subjects were instructed to tap as rapidly as possible. For most of the tests, there were 20 subjects who had Fugl-Meyer scores available for correlation, and 24 subjects with NIH scores; these values are reported in the first column of Table 1 as n.

Table 1 shows the degree of correlation between various motor behavior tasks measured using the digital motor event recording system and the three scales listed above: the Fugl-Meyer arm motor scale (FM), a hand subscore of the Fugl-Meyer arm motor scale (FM hand), and the NIH stroke scale (NIH). The first two measure only motor deficits, whereas the NIH stroke scale is sensitive to abnormalities in a wide range of neurological modalities, including motor, sensory, language, vision, and more. Each of these scales was correlated with digital measurements. Displayed are the r values (i.e., Spearman's rho, or correlation coefficient), and the p value (probability) for

TABLE 1

Table of Correlation Coefficients (r) with Respective p Values by motor performance parameter and by neurologic scale

| Parameter | r--FM 20 pts | p--FM, slope 20 pts | r--FM hand, 20 pts | p--FM hand, slope 20 pts | r--NIH, 24 pts | p--NIH, slope 24 pts | r--FM 11 Box pts | p--FM, slope 11 Box pts | r--FM hand 11 Box pts | p--FM hand slope 11 Box pts | r--NIH 11 Box pts | p--NIH, slope Box 11 pts |
|---|---|---|---|---|---|---|---|---|---|---|---|---|
| Par/G Fast squeeze: Mean frequency n = 20FM/24NIH | 0.693 | 0.0007 | 0.741 | 0.0002 | 0.577 | 0.0031 | — | — | — | — | | |
| Par/G Fast squeeze: Mean force n = 20FM/24NIH | 0.877 | <.0001 | 0.85 | <.0001 | 0.742 | <.0001 | — | — | — | — | | |
| Par/G Fast squeeze (Mean | 0.814 | <.0001 | 0.806 | <.0001 | 0.756 | <.0001 | — | — | — | — | | |

TABLE 1-continued

Table of Correlation Coefficients (r) with Respective p Values
by motor performance parameter and by neurologic scale

| Parameter | r--FM 20 pts | p--FM, slope 20 pts | r--FM hand, 20 pts | p--FM hand, slope 20 pts | r--NIH, 24 pts | p--NIH, slope 24 pts | r--FM 11 Box pts | p--FM, slope 11 Box pts | r--FM hand 11 Box pts | p--FM hand slope 11 Box pts | r--NIH 11 Box pts | p--NIH, slope Box 11 pts |
|---|---|---|---|---|---|---|---|---|---|---|---|---|
| frequency × Mean force) n = 20FM/24 NIH | | | | | | | | | | | | |
| Right Hand Fast squeeze (Mean frequency × Mean force) n = 20FM/24NIH | 0.077 | .75 | 0.022 | .93 | 0.237 | .26 | — | | — | | — | |
| Left Hand Fast squeeze (Mean frequency × Mean force) n = 20FM/24NIH | 0.164 | .49 | 0.184 | .44 | 0.152 | .48 | — | | — | | — | |
| Par/G Fast squeeze: Coefficient of Variation of frequency n = 19FM/23NIH | 0.249 | .31 | 0.253 | .29 | 0.327 | .13 | — | | — | | — | |
| Paretic Sustained squeeze: Maximum force n = 20FM/24NIH | 0.701 | .0006 | 0.68 | .001 | 0.612 | .0015 | — | | — | | — | |
| Par/G Sustained squeeze: Maximum force n = 20FM/24NIH | 0.872 | <.0001 | 0.879 | <.0001 | 0.755 | <.0001 | — | | — | | — | |
| Par/G Sustained squeeze: Force at 5 seconds/Maximum Force n = 20FM/24NIH | 0.447 | .0496 | 0.469 | .037 | 0.329 | .12 | — | | — | | — | |
| Par/G Sustained squeeze: integral of Force over first 5 seconds n = 20FM/24NIH | 0.85 | <.0001 | 0.83 | <.0001 | 0.8 | <.0001 | — | | — | | — | |
| Par/G Sustained squeeze: time to reach maximum Force n = 20FM/24NIH | 0.077 | .74 | 0.055 | .81 | 0.276 | .19 | — | | — | | — | |
| Par/G Index Finger Mean frequency n = 17FM/20NIH | 0.636 | .0061 | 0.683 | .0025 | 0.458 | .042 | 0.775 | .0089 | 0.817 | .0039 | 0.397 | .256 |
| Paretic Index Finger Mean frequency n = 18FM/21NIH | 0.498 | .0358 | 0.587 | .0103 | 0.41 | .0652 | 0.539 | .0876 | 0.646 | .032 | 0.253 | .45 |
| Par/G Index Finger Frequency: Coefficient Of Variation n = 17FM/20NIH | 0.158 | .55 | 0.045 | .87 | 0.212 | .37 | 0.535 | .111 | 0.519 | .124 | 0.503 | .138 |
| Par/G (Sustained squeeze maximum Force) × (Index finger Mean frequency) n = 17FM/20NIH | 0.76 | .0004 | 0.784 | .0002 | 0.669 | .0013 | 0.891 | .0005 | 0.861 | .0014 | 0.701 | .0239 | the significance of the slope of this correlation. One hundred times the square of the quantity r provides the percentage of a change in x that can be explained by a change in y (r ranges from 0 to 1). In Table 1, x and y are the traditional score and the normalized score obtained from the digital motor event recording system, respectively. The probability that a given value of r could arise by chance if no correlation actually existed between x and y is equal to p (p also ranges from 0 to 1). Thus, a value of r close to 1 and a value of p close to 0 indicate, with high confidence, a strong correlation. The initial results with index finger tapping disclosed divergent motor strategies, such as movements of the shoulder, elbow, or wrist which complemented index finger tapping. To obtain a more uniform tapping behavior, the last eleven subjects entered into the study were tested with the active arm strapped to a frame, restricting movement to the index finger metacarpophalangeal joint (the knuckle). A separate analysis of the data from these eleven subjects appears in the right half of Table 1 for selected parameters.

A significant (p<0.05) correlation was found for the whole group and each of the three scores for the following parameters:

Par/G fast squeeze: mean frequency

Par/G fast squeeze: mean force

Par/G fast squeeze (mean frequency×mean force)

Paretic sustained squeeze: maximum force

Par/G sustained squeeze: maximum force

Par/G sustained squeeze: force at 5 seconds/maximum force [Fugl-Meyer arm score significant only]

Par/G sustained squeeze: integral of force over first 5 seconds

Par/G index finger mean frequency

Paretic index finger mean frequency [Fugl-Meyer hand subscore only]

Par/G (sustained squeeze maximum force)×(index finger mean frequency)

The correlation coefficient with the Fugl-Meyer scores was improved with introduction of the restraining strap for the following parameters:

Par/G index finger mean frequency

Paretic index finger mean frequency

Par/G index finger frequency: coefficient of variation

Par/G (sustained squeeze maximum Force)×(index finger mean frequency)

Several conclusions were drawn from these findings. Squeezing and tapping data obtained with the digital motor event recording system had a good correlation with traditional measures of neurologic function. Each traditional scale requires at least 15 minutes to perform, whereas data acquisition with the digital motor event recording system required less than one minute to record data, and 2 to 4 minutes to process it with the software used in the study.

Use of normalized measurements for individual motor function variation improved the degree and significance of the correlations. As shown in Table 1, correlations were weaker with use of a parameter from a single hand (e.g. right, left, or paretic) than the Par/G ratio of paretic hand/good hand.

In most cases, squeezing had better correlation with the Fugl-Meyer score for the entire arm, and tapping had better correlation with the Fugl-Meyer subscore for the hand in this group of subjects. This internal consistency underscored the specificity of the findings.

Mirror movements were noted in all but four of the subjects with stroke during measurement of squeezing. Previously, mirror movements have been measured using either electromyography (EMG) to document muscle activity, or using bedside descriptive gradings (e.g., mild-severe). The digital motor event recording system permitted quantitation of mirror movements.

Utilizing the capability of the digital motor event recording system to measure multiple motor activities, analysis of the product of two different tasks was performed, such as the parameter Par/G (sustained squeeze maximum force)×(index finger mean frequency). This summary product should provide new insights into motor function.

Furthermore, use of the digital motor event recording system permits analyses of motor function not possible with traditional scales. A number of features of a motor behavior, such as integration of force over time, can be derived once the performance is digitized and recorded. This was demonstrated by the sustained squeeze analysis. For a sustained squeeze lasting five seconds, both the total force and the maximum force correlated well with the neurological scales. The total force is defined by the integral of force over the five seconds. However, a significant correlation was not found in this group of subjects with the decay in force, represented as the force at 5 seconds divided by the maximum force. The time to reach maximum force also did not achieve significant correlation in this group.

Through analysis of the parameters indicated, obtained from the digitized sustained squeeze data, a broader picture of post-stroke motor function emerged. Regardless of the rate of force generation or dissipation, the peak force remained a good reflection of neurologic status, as defined by the Fugl-Meyer and NIH scale values. Likewise, regardless of the time for onset or decay, the total amount of work performed during hand squeezing (i.e., the integral of the force) correlated well with neurologic status. The results of testing are shown in the graphs of FIGS. 5 through 16.

Example 1a

Squeezing

Figure 5:
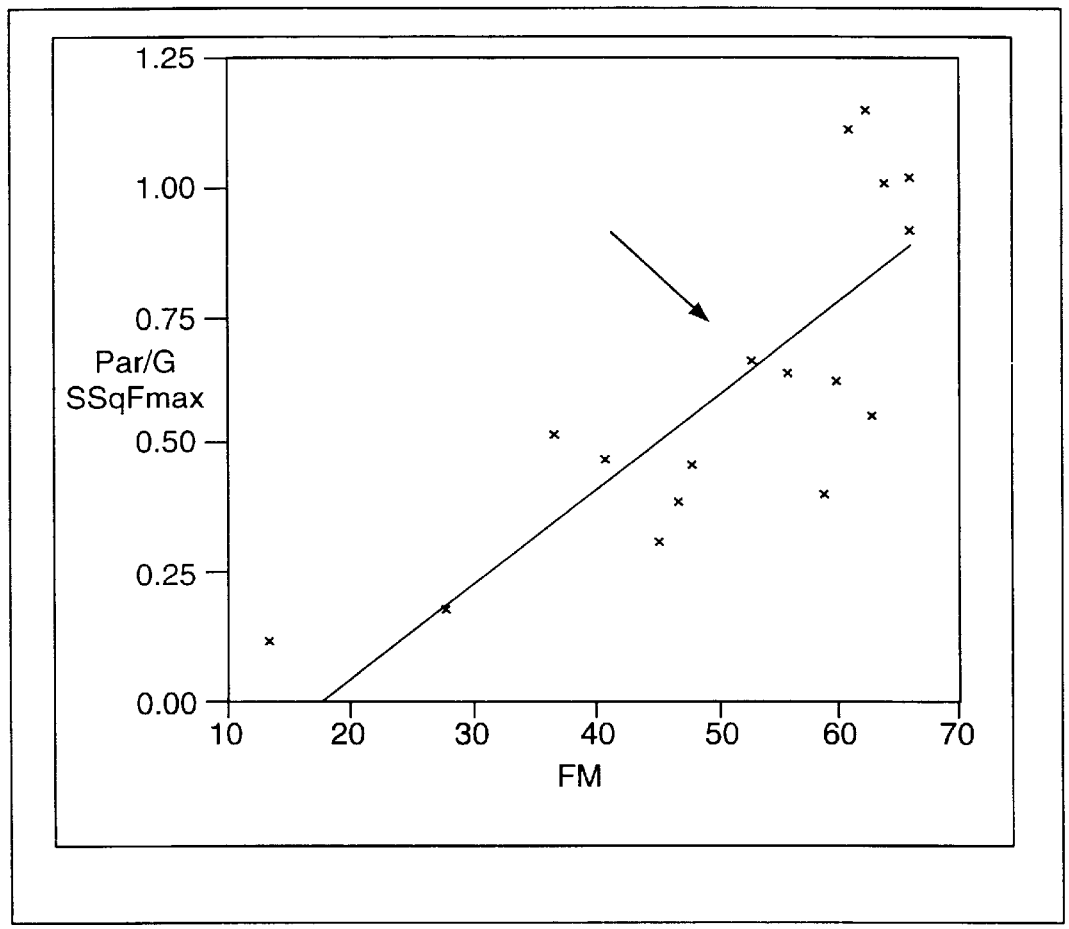
FIG. 5 is a plot showing the correlation of Fugl-Meyer arm motor score with normalized motor scores for sustained squeezing obtained with the disclosed device, as well as statistical data pertaining to this comparison.

FIG. 5 shows the scatterplot and respective statistics for 20 subjects performing sustained squeezing, as correlated with the Fugl-Meyer arm motor score. The arrow indicates the data point from one specific subject who sustained a left-sided stroke 14 days prior to examination, causing weakness of the right side. His Fugl-Meyer arm motor score was 53 out of 66 on the right (paretic) side. Thus he had a moderate deficit (66 is "normal"). The record of this subject's motor performance, shown as graphs of sustained squeezing, appear in FIGS. 6A and 6B and 7A and 7B. The parameter values obtained from this record are displayed in Table 2, below.

In FIG. 5, x=Fugl-Meyer score and y=maximum force of normalized sustained squeeze. The equation printed next to "Linear Fit" is the linear equation for the line which was determined to best fit the data, in the form y=b+mx, where m =slope, and b=y-intercept. The values of m and b are of little importance; more significant are "RSquare", which indicates that $r^2$=0.76 and "Prob>|t|", which indicates that $p<0.0001$.

Figures 6A, 6B:
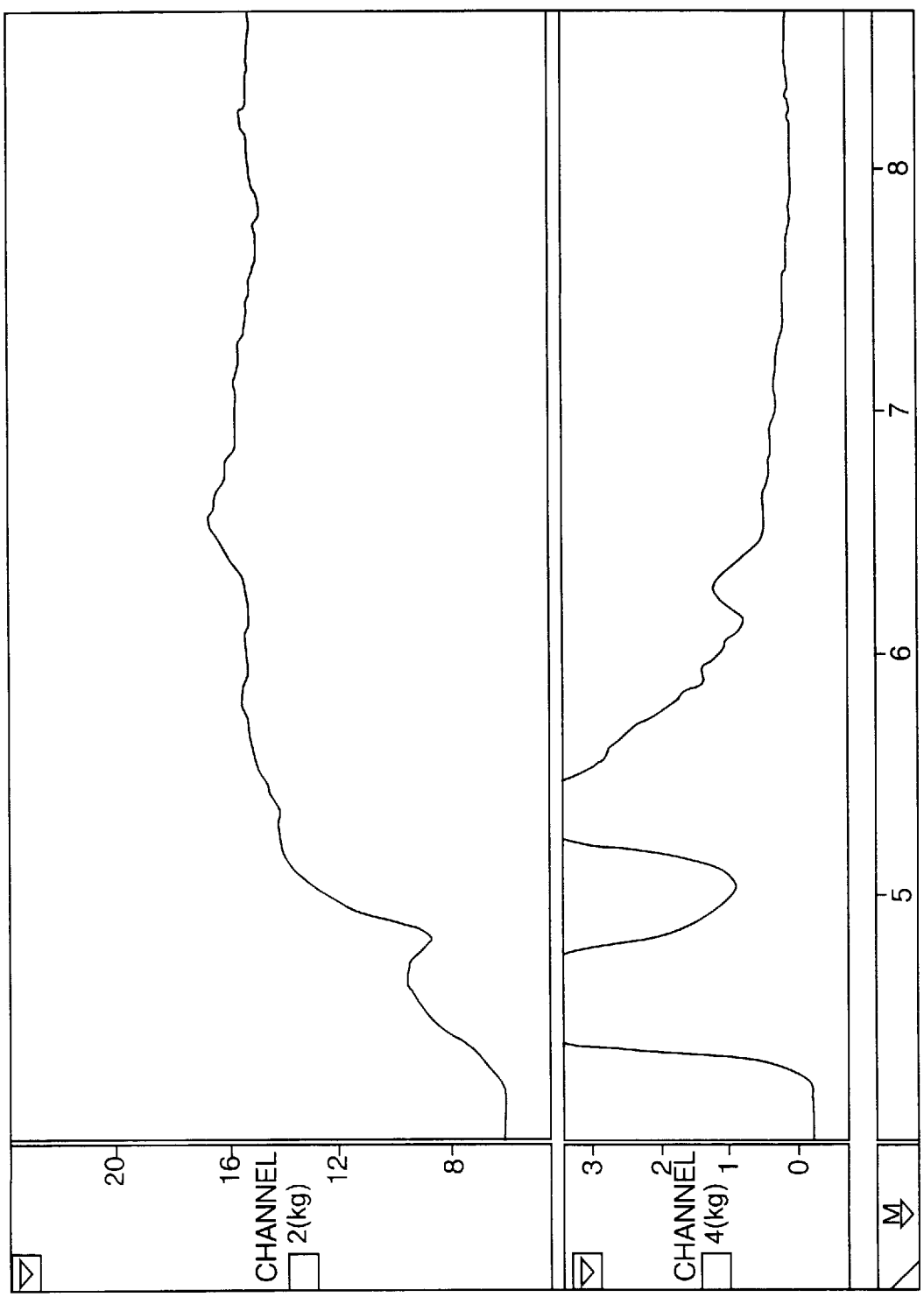
FIGS. 6A and 6B are plots of the record of a stroke patient's squeezing a transducer in the paretic hand (6A) and corresponding mirror movements recorded simultaneously with a transducer in the good hand (6B).

FIGS. 6A and 6B show the record of the subject's performance in right (paretic) hand squeezing: FIG. 6A, right (paretic) hand squeeze; FIG. 6B, left (good) hand instructed to be at rest. FIGS. 7A and 7B show the record Table 2. Parameter Values Obtained From the Sustained Squeeze Recordings in FIGS. 7a and 7b

TABLE 2

Parameter Values Obtained From the Sustained Squeeze Recordings in FIGS. 7a and 7b

| Parameter | Value |
|---|---|
| Maximum Force, R | 10.46 |
| Maximum Force, L | 15.3 |
| Time to reach maximum force, R | 2.36 |
| Time to reach maximum force, L | 1.38 |
| Integral of force generated in 5 seconds, R | 20.36 |
| Integral of force generated in 5 seconds, L | 63.06 |
| Force present at 5 seconds, R | 9.7 |
| Force present at 5 seconds, L | 12.15 |
| Par/G maximum force | 0.68366 |
| Par/G force at 5 seconds/maximum force | 0.927342 |
| Par/G integral of force generated in 5 seconds | 0.322867 |
| Par/G time to reach maximum force | 0.710145 | of the subject's performance in left (good) hand squeezing: FIG. 7A, left (good) hand squeeze; FIG. 7B, right (paretic) hand instructed to be at rest. The presence of the mirror movements are most pronounced in FIGS. 6A and 6B when the left (good) hand (6B) is squeezing unintentionally during planned movement of the right (paretic) hand (6A). The y-axis is force measured in kilograms (see above). The x-axis is time measured in seconds.

Example 1b

Tapping

Figure 8:
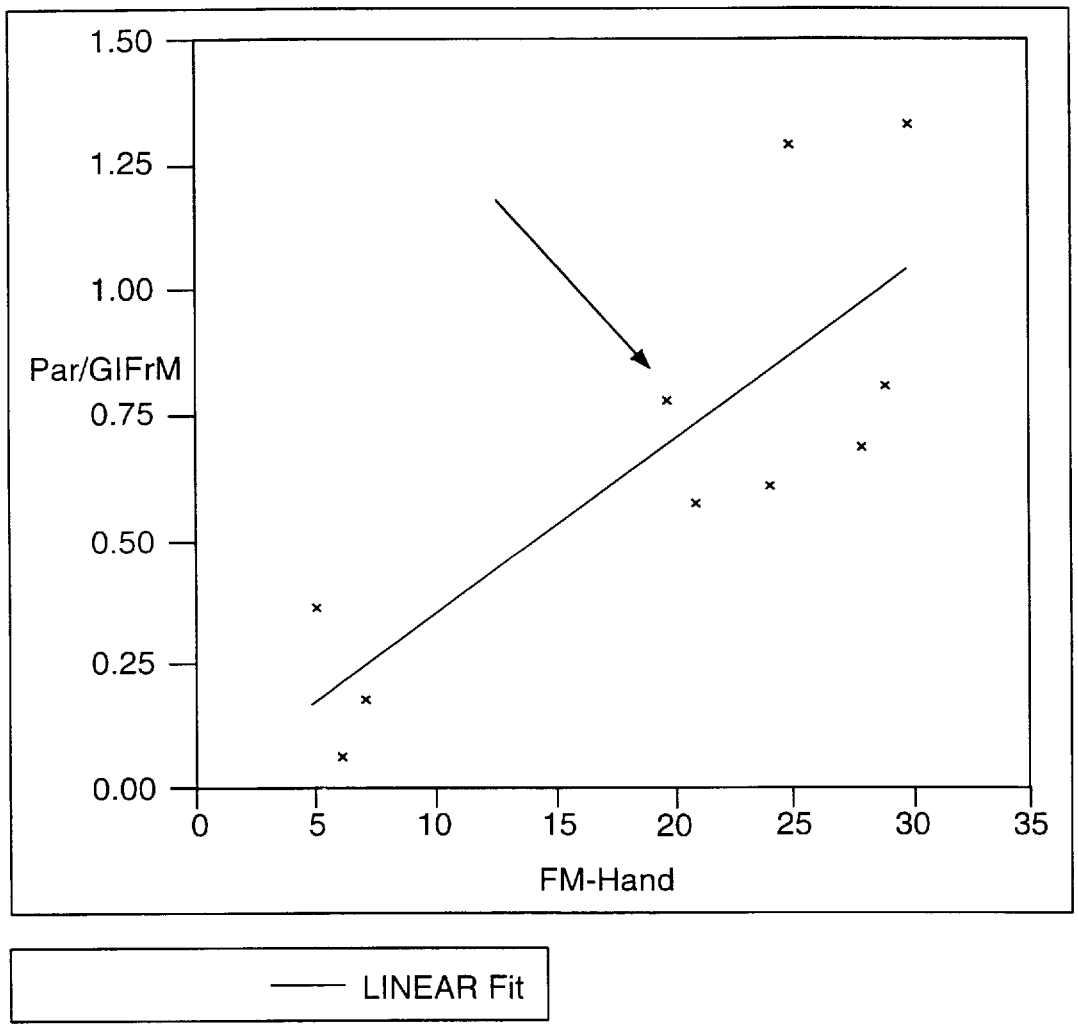
FIG. 8 is a plot showing correlation of Fugl-Meyer hand motor subscore with normalized motor scores for index finger tapping obtained with the disclosed device, as well as statistical data pertaining to this comparison.

FIG. 8 shows a scatterplot and respective statistics for eleven subjects performing index finger tapping using a frame, as correlated with the Fugl-Meyer hand motor subscore. This plot should be interpreted as per FIG. 5; x=Fugl-Meyer hand motor subscore and y=normalized mean frequency for index finger tapping. The arrow indicates the data point from one specific subject who sustained a right-sided stroke one year prior to examination, causing persistent weakness of the left side. His Fugl-Meyer hand subscore was 20 out of 30 on the left (paretic) side. This suggests a moderate deficit (30 is "normal"). This subject's finger tapping performance is graphed in FIGS. 9A and 9B and 10A and 10B. His index tapping mean frequency was 4.14±0.54 Hz (mean ± SD) on the right (good) side and 3.28±0.22 Hz on the left (paretic) side.

Figures 10A, 10B:
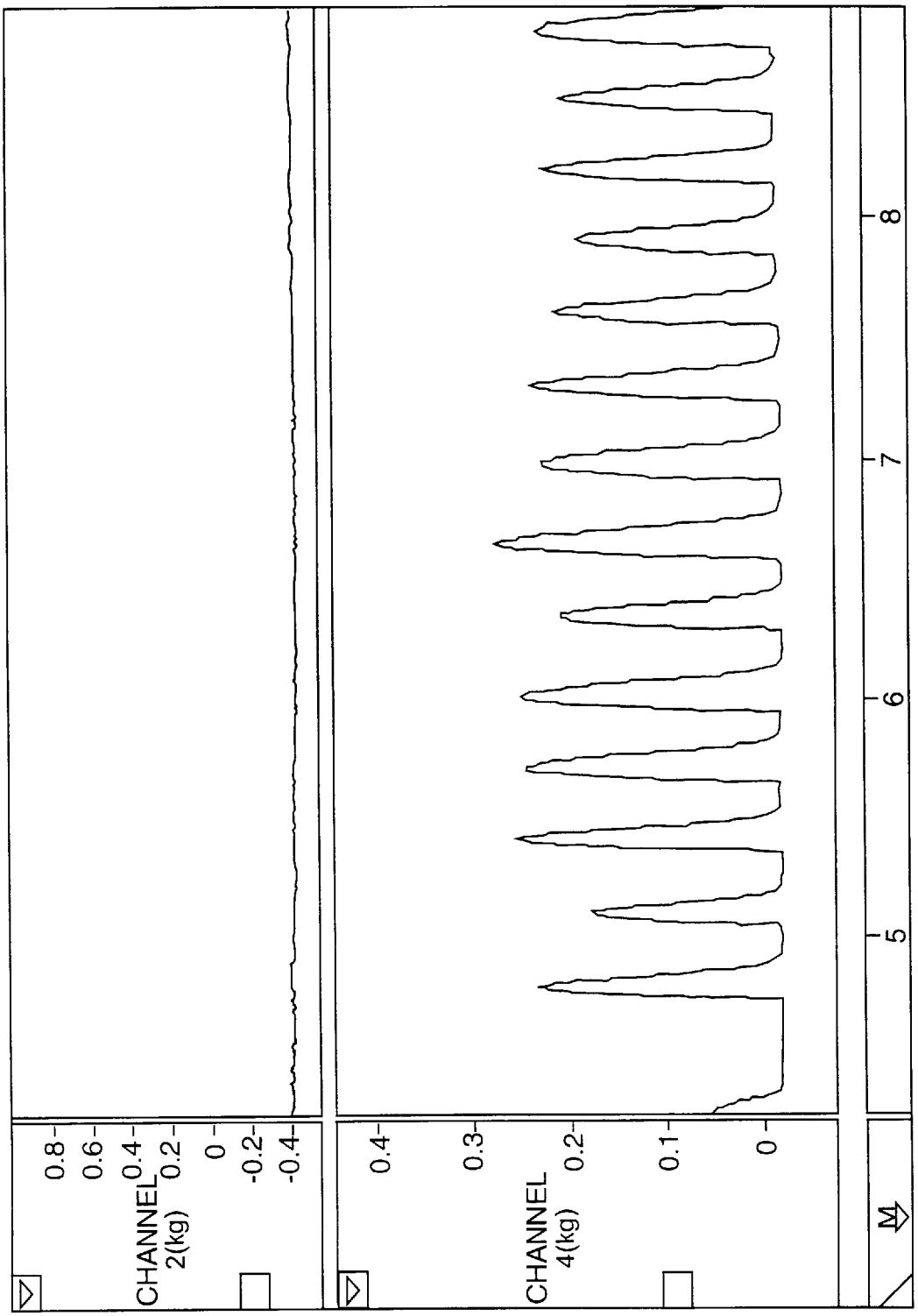
FIGS. 10A and 10B are plots of the record of a stroke patient's index finger tapping a transducer with the paretic hand (10B) and corresponding mirror movements recorded simultaneously with a transducer in the palm of the good hand (10A).

FIG. 9B shows the digitized graph of the index finger tapping for the subject's right (good) hand, while FIG. 9A shows the left (paretic) hand at rest while holding a transducer (no mirror movements). FIG. 10B shows the graph of left (paretic) index finger tapping in the bottom panel. No mirror movements are apparent in FIG. 10A, which shows the right index finger at rest. Although these plots appear quite similar to the eye, the computerized analysis determined that the mean frequency of tapping with the left (paretic) hand was only about 75% of the mean frequency of tapping with the right (good) hand.

EXAMPLE 2

Spectral Analysis of Data

A 66 year old right-handed male was analyzed with the digital motor event recording device described above, one day after suffering a right prefrontal cortical cerebrovascular accident (CVA).

The results presented in FIGS. 11A to 11C and 12A to 12C were obtained from the four-finger tapping analysis of the right (good) and left (paretic) hands, respectively. Four finger tapping (all fingers except the thumb) is a movement that occurs at the wrist. The raw data from the right (good) hand (see FIG. 11A) indicated regular, rhythmic tapping with fairly constant amplitude. The data produced by the left (paretic) hand (see FIG. 12B), however, was comparatively irregular, both in frequency and amplitude. Fourier transforms of the raw data highlighted these differences (FIGS. 11C and 12C).

For the right (good) hand (FIG. 11A), the frequency distribution is sharp and narrow (note that other peaks are simply harmonics, occurring at 2f, 3f, and so on, where f=frequency), indicating little variation. His tapping frequency was 5.4±0.2 Hz (mean ± SD), with a coefficient of variation of 4.

For the left (paretic) hand (FIG. 12B), the distribution is flat and broad, indicating greater variation. The frequency was 4.9±0.5 Hz (mean±SD), with a coefficient of variation of 10. Thus, the mean tapping frequency was lower and the standard deviation and coefficient of variation were greater for the paretic hand than for the good hand.

Differences were also noted in the corresponding mirror movements (see FIGS. 11B and 12A). The data showed significant mirror activity in the right (good) hand while the left (paretic) hand tapped. In contrast, the mirror activity in the left (paretic) hand during the tapping of the while the right (good) hand was absent.

Figure 13:
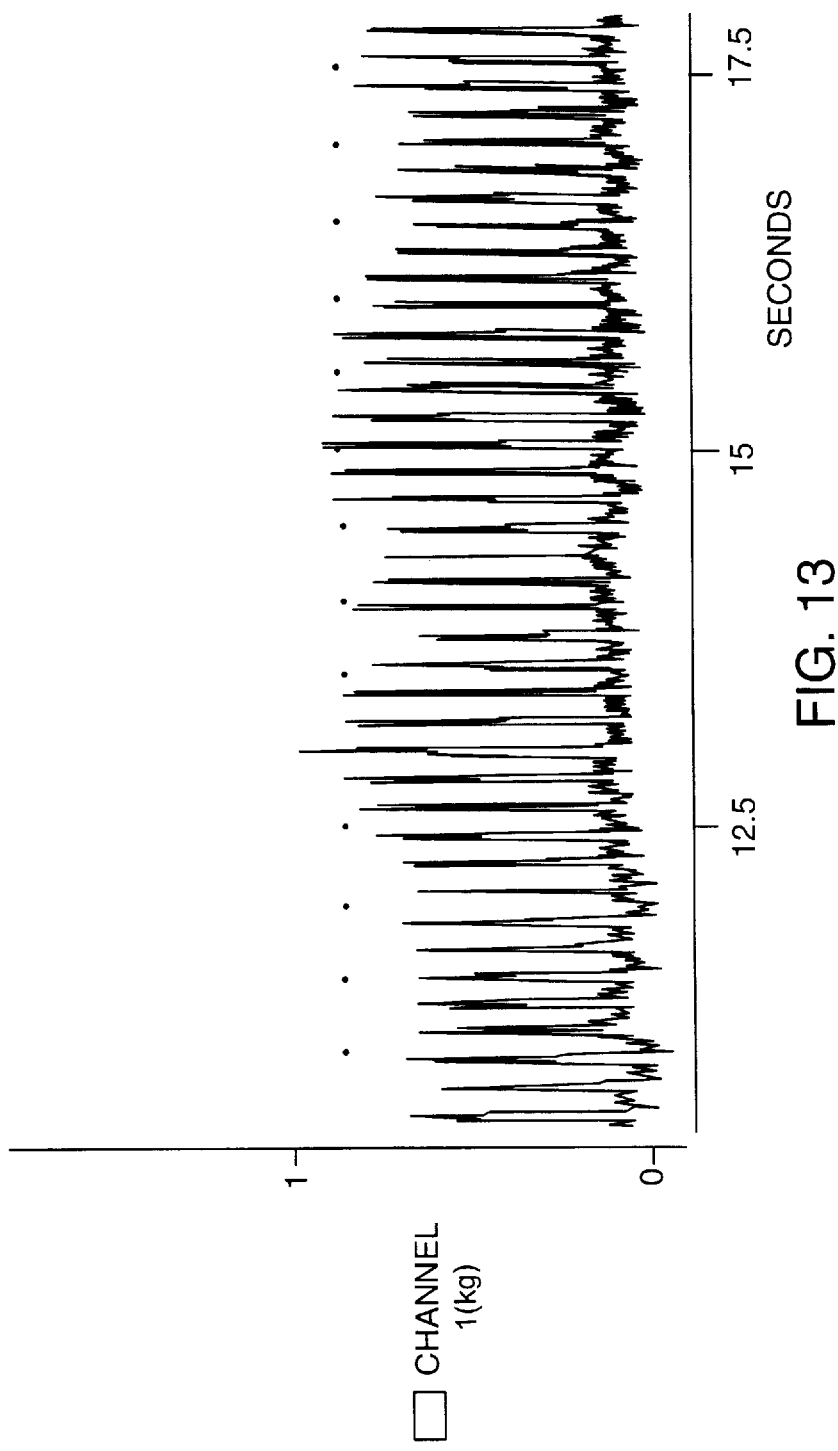
FIG. 13 is a plot of the record of a stroke patient's tapping a transducer with the index finger of the good hand.
Figure 14:
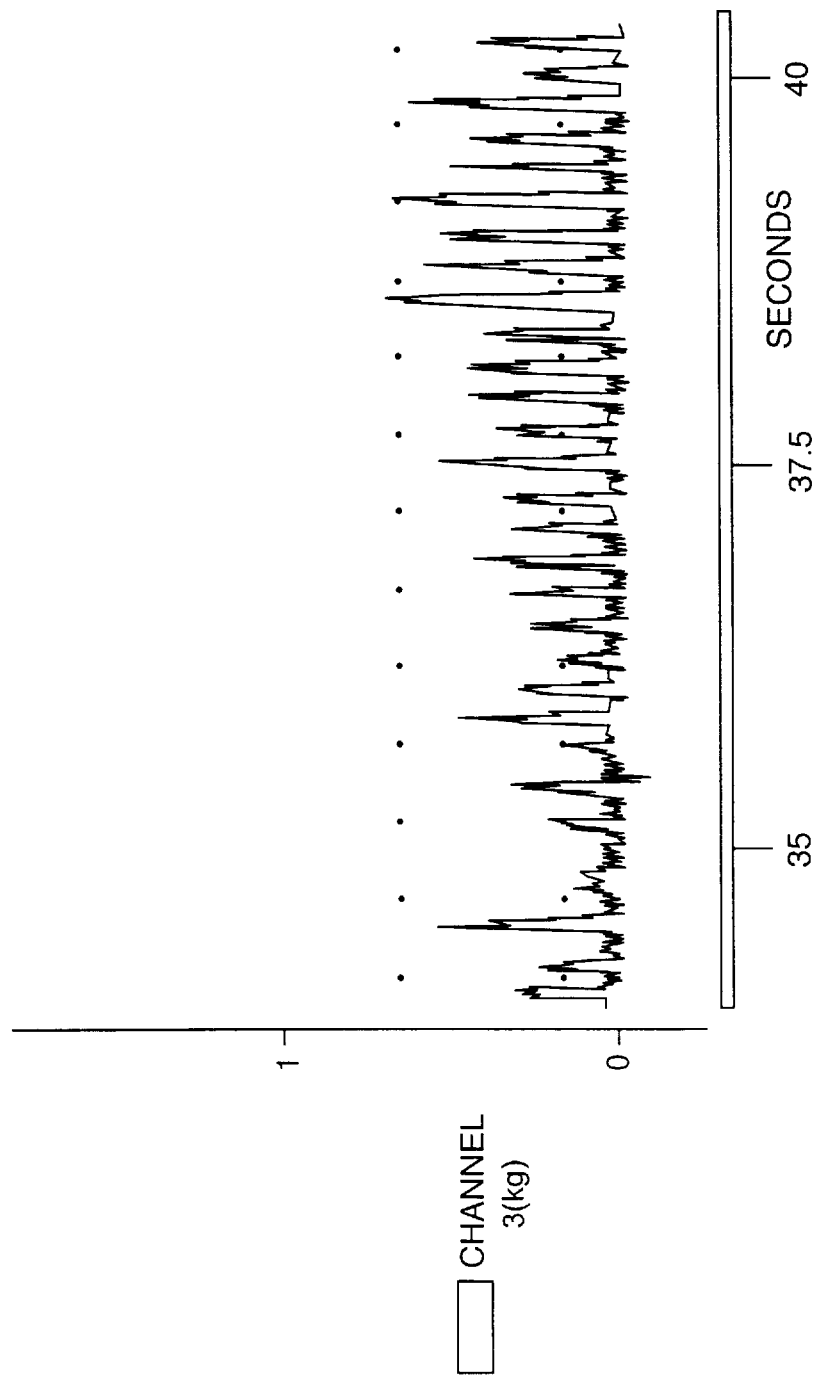
FIG. 14 is a plot of the record of a stroke patient's tapping a transducer with the index finger of the paretic hand.
Figure 15A:
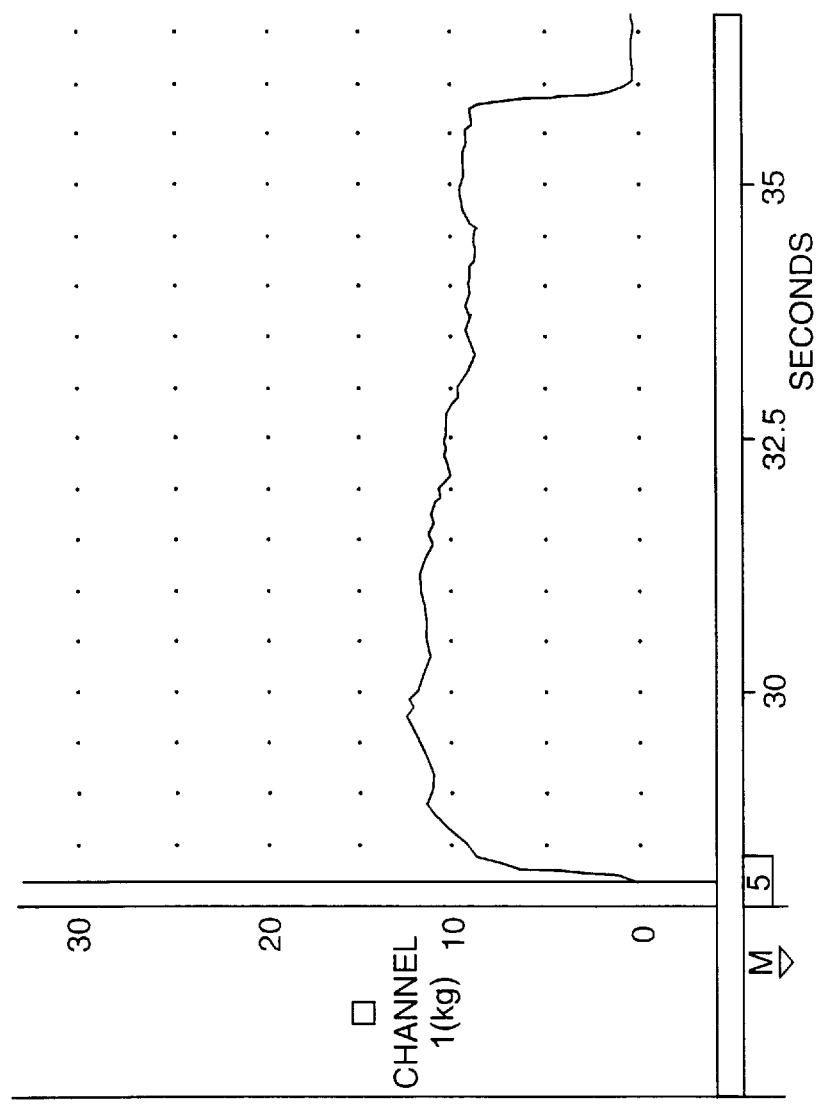
FIGS. 15A and 15B are plots of the record of a stroke patient's squeezing a transducer with paretic (15A) and good (15B) hands (separately, not simultaneously), one day post-stroke.
Figure 15B:
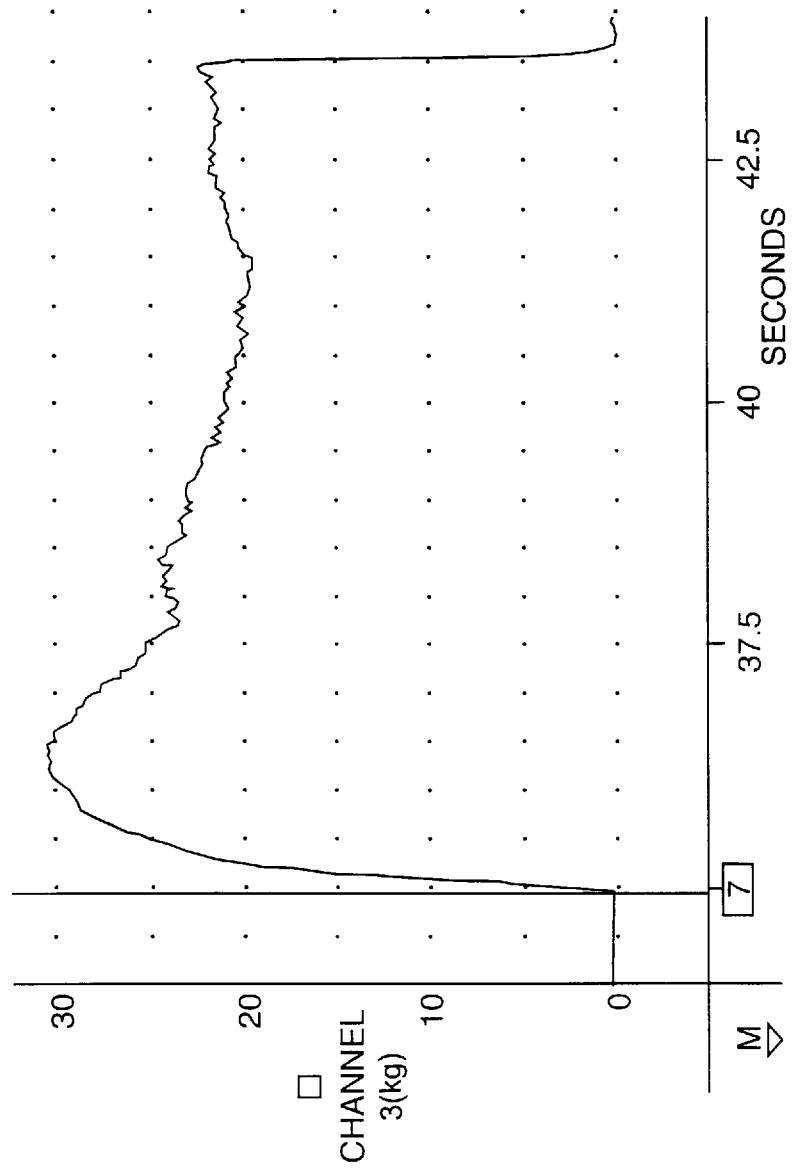

Similar results were obtained from single-finger tapping tests of the good and paretic hands, as indicated in FIGS. 13 and 14, respectively. For the right (good) hand, the tapping frequency was 5.4±0.2 Hz (mean±SD), with a coefficient of variation of 4; with the left (paretic) hand, the subject tapped with a frequency of 4.9±0.7 Hz (mean±SD), with a coefficient of variation of 14.

EXAMPLE 3

Serial Studies of Motor Function

A 68 year old right-handed male was analyzed with the digital motor event recording device described above, one day after suffering a left frontoparietal cortical CVA which produced right sided weakness. He was examined again six days after the stroke.

At the time of the first test (FIGS. 15A and 15B), the maximum force and the integral of total force were both diminished in the right (paretic) hand (FIG. 15A)(12.3 kg and 58.7 kg.s, respectively) as compared to the left (good) hand (FIG. 15B)(30.5 kg and 121.5 kg.s, respectively). It should be noted that the subject's Fugl-Meyer score of 47 correlates well with his normalized ratio of (12.3)÷(30.5)= 0.40, as indicated in FIG. 5.

Figure 16B:
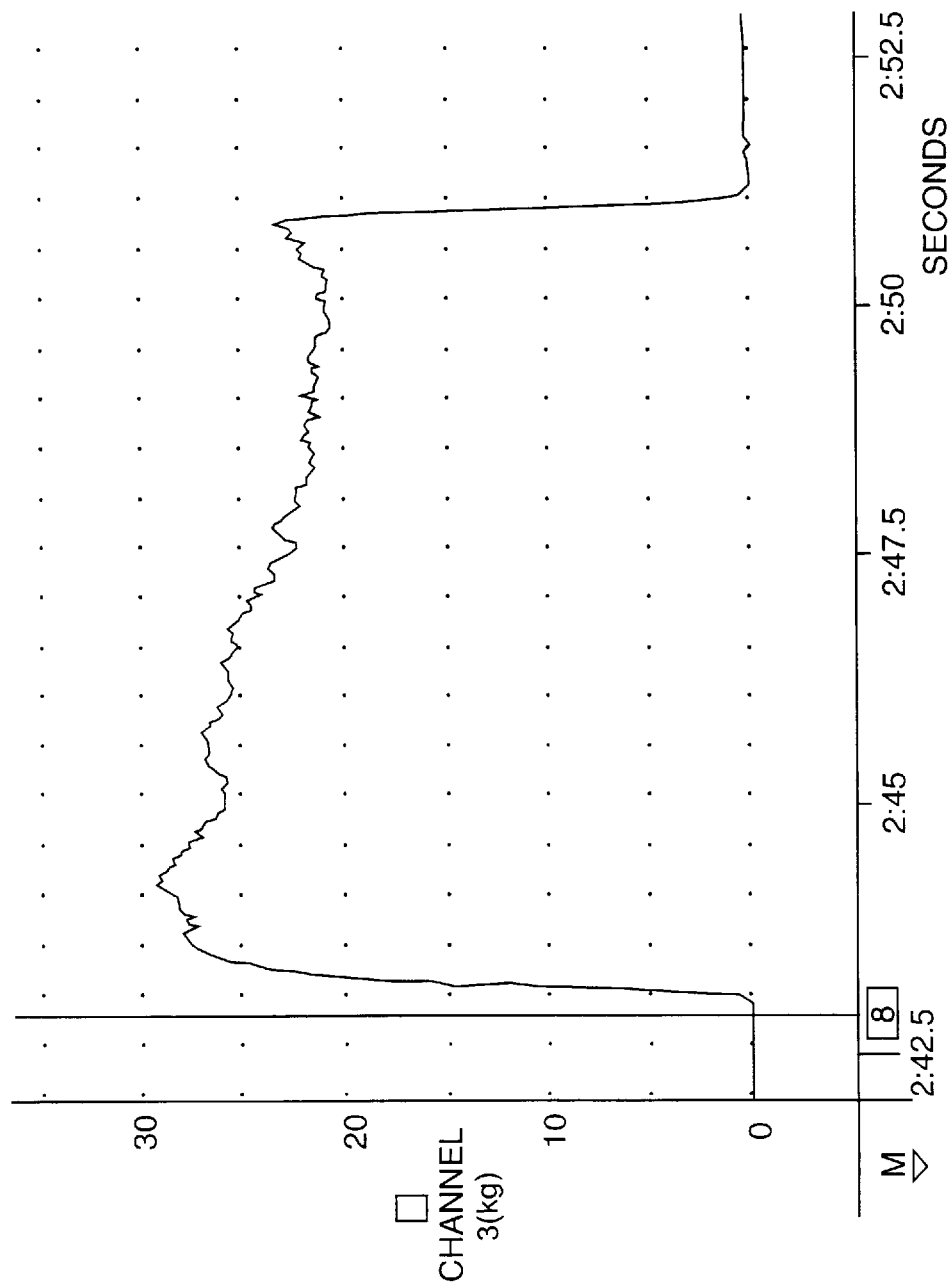

Repeat testing five days later, six days after the stroke, revealed improvement in both parameters for sustained squeezing (FIGS. 16A and 16B). Respective maximum force and integral of total force values were 27.5 kg and 110.5 kg.s for the right (paretic) hand (FIG. 16A), and 29.5 kg and 122.6 kg.s for the left (good) hand (FIG. 16B).

EXAMPLE 4

Assessment of Non-CVA Subjects

Subjects exhibiting variation in motor ability due to causes other than stroke are also assessed with the digital motor event recording system. For example, patients having cerebellar degeneration are characterized by inconsistent production of force by the hands, both in squeezing and tapping, as measured at set intervals of days or weeks. Parkinson's disease patients have difficulty producing strong taps. Arthritis patients, and patients recovering from surgical procedures exhibit deficits in power or speed, or both, when tapping or squeezing. The digital motor event recording system allows the progress, either improvement or degeneration, of these conditions to be monitored.

EXAMPLE 5

Latency Study

A subject is fitted with EMG leads and is instructed to squeeze a transducer as described above. The recording is analyzed to determine whether or not a latency period is detectable, i.e., a lag between the time the EMG leads detect a signal and the time of force production. The analysis is repeated for tapping. Testing with a large number of subjects allows correlations between latency and various disease states, if any, to be established.

EXAMPLE 6

Drug Efficacy Studies

The tapping and squeezing abilities of a subject undergoing therapy with a drug for the treatment of arthritis are measured at set intervals over several weeks or months using the digital motor event recording system. The history of recordings is analyzed to determine whether or not the subject's power and speed are improving.

Other Embodiments

It is to be understood that while the invention has been described in conjunction with the detailed description thereof, that the foregoing description is intended to illustrate and not limit the scope of the appended claims. Other aspects, advantages, and modifications are within the scope of the following claims.

For example, electromyography data can be entered using the proper leads. Different transducers could be used to enter other forms of information, including temperature, sound, blood pressure, or range of motion. In addition, the system can be capable of playing a message (e.g., of a voice issuing standard instructions) or music, or turning on an external electrical device.

What is claimed is:

1. An apparatus for measuring a set of repetitive, individual motor events of a subject, wherein the motor events have a frequency and a force component, said apparatus comprising:

(a) a transducer, adapted to generate an analog signal corresponding to frequency and force of the subject's repetitive motion;

(b) an amplifier, connected electrically to said transducer, which amplifies said analog signal;

(c) an analog-to-digital converter, connected electrically to said amplifier, which converts said analog signal into a digital signal; and (d) a computer, connected electrically to said analog-to-digital converter, wherein said computer is programmed to:
(e)(i) receive said digital signal as input;
(e)(ii) store said digital signal for subsequent retrieval;
(e)(iii) retrieve said stored digital signal for processing;
(e)(iv) process said stored digital signal, wherein said processing comprises the measurement of:
(f)(i) the mean force amongst the set of individual motor events over time; and
(f)(ii) the mean frequency of the set of individual motor events over time.

2. The apparatus of claim 1, wherein said transducer is adapted to generate an analog signal when the subject taps the transducer with a finger.

3. The apparatus of claim 1, wherein said transducer is adapted to generate an analog signal when the subject squeezes the transducer with a hand.

4. The apparatus of claim 1, wherein said processing further comprises the measurement of the integral of the force of the individual motor events over a predetermined time interval.

5. The apparatus of claim 1, wherein said processing further comprises the measurement of the coefficient of variation of the force amongst the set of individual motor events.

6. The apparatus of claim 1, wherein said processing further comprises the measurement of the coefficient of variation of the frequency amongst the set of individual motor events.

7. The apparatus of claim 1, wherein said processing further comprises the measurement of the maximum force amongst the set of individual motor events.

8. The apparatus of claim 1, wherein said processing further comprises the measurement of the duration of individual motor events.

9. The apparatus of claim 1, wherein said apparatus further comprises:
a second transducer, electrically connected to said computer, said second transducer being adapted to generate a second analog signal corresponding to frequency and force of a second repetitive motor event of the human subject.

10. The apparatus of claim 9, wherein said first and second signals are obtained simultaneously.

11. The apparatus of claim 9, wherein said first and second signals are obtained at different times.

12. The apparatus of claim 9, wherein said processing further comprises calculating the ratio of the force and frequency determined by processing the first signal to the force and frequency determined by processing the second signal.

13. The apparatus of claim 2, wherein said transducer is mounted within a frame, said frame comprising:
an armrest, which allows the subject's arm to be positioned in the same location for each finger tap;
a retaining strap connected to the armrest to prevent movement of the subject's arm during finger tapping and to isolate movement to the finger; and
a slot which receives and secures the transducer, preventing motion of a base of the transducer, wherein said slot is located adjacent to said armrest so as to allow the subject's finger to contact the transducer.

14. The apparatus of claim 1, further comprising a plurality of electromyography leads, electrically connected to said computer.

15. The apparatus of claim 1, further comprising a plurality of input devices, electrically connected to said computer, wherein said input devices are independently capable of detecting stimuli selected from the group consisting of temperature, blood pressure, sound, and range of motion.

16. An apparatus for measuring a force produced by a single motor event of a subject over an extended period of time, said apparatus comprising:
(a) a transducer, adapted to generate an analog signal when the subject produces a force over an extended period of time;
(b) an amplifier, connected electrically to said transducer, which amplifies said analog signal;
(c) an analog-to-digital converter, connected electrically to said amplifier, which converts said analog signal into a digital signal; and
(d) a computer, connected electrically to said analog-to-digital converter, wherein said computer is programmed to:
(e)(i) receive said digital signal as input;
(e)(ii) store said digital signal as a stored signal for subsequent retrieval;
(e)(iii) retrieve said stored digital signal for processing;
(e)(iv) process said stored digital signal, wherein said processing comprises measuring the force at multiple time points during the extended period of time, and calculating an integral of force over the extended period of time.

17. The apparatus of claim 16, wherein said transducer is adapted to generate an analog signal when a subject performs a sustained squeeze with a hand.

18. The apparatus of claim 16, wherein said processing further comprises the measurement of the integral of the force produced over the duration of the motor event.

19. The apparatus of claim 16, further comprising a second transducer, electrically connected to said computer, said second transducer being adapted to generate a second analog signal when the subject produces a second force over an extended period of time.

20. The apparatus of claim 19, wherein said first and second signals are obtained simultaneously.

21. The apparatus of claim 19, wherein said first and second signals are obtained at different times.

22. The apparatus of claim 19, wherein said processing further comprises calculating a maximum force, and a time course for each signal over the duration of the motor event.

23. The apparatus of claim 19, wherein said processing further comprises calculating the ratio of the force determined by processing the first signal to the force determined by processing the second signal.

24. The apparatus of claim 16, further comprising a plurality of electromyography leads, electrically connected to said computer.

25. The apparatus of claim 16, further comprising a plurality of additional input devices, electrically connected to said computer, wherein said input devices are capable of detecting stimuli selected from the group consisting of temperature, blood pressure, sound, and range of motion.

26. A method of analyzing a motor event of a subject, said method comprising:
obtaining at intervals of time an analog signal proportional to the intensity of said subject's exertion of force on a transducer;
amplifying said analog signal to make an amplified analog signal;
converting said amplified analog signal to a digital signal; and processing said digital signal; wherein said processing comprises analyzing the waveform of said signal to obtain frequency and amplitude data.

27. The method of claim 26, wherein said transducer is placed within an MRI instrument, such that the transducer can be actuated by the subject during the course of an MRI session.

28. The method of claim 26, further comprising measuring electromyography lead signals with a plurality of electromyography leads electrically connected to said computer.

29. The method of claim 28, further comprising comparing the timing of signals generated by the transducers and signals generated by the electromyography leads.

30. The method of claim 26, further comprising simultaneously monitoring contralateral motor events with the aid of a second transducer electrically attached to said computer.

31. The method of claim 30, further comprising dividing parameters or moments pertaining to activity of a body part with abnormality of movement by the corresponding parameters or moments pertaining to activity of the contralateral body part without abnormality of movement.

32. A method of analyzing a motor event of a subject over an extended period of time, said method comprising:

obtaining at intervals of time an analog signal proportional to the intensity of said subject's exertion of force on a transducer;

amplifying said analog signal to make an amplified analog signal;

converting said amplified analog signal to a digital signal; and processing said digital signal; wherein said processing comprises measuring the force at multiple time points during the extended period of time, and calculating an integral of force over the extended period of time.

* * * * *